United States Patent [19]

Van Wauwe et al.

[11] Patent Number: 4,931,444

[45] Date of Patent: Jun. 5, 1990

[54] 5-LIPOXYGENASE INHIBITING 4-(4-PHENYL-1-PIPERAZINYL)PHENOLS

[75] Inventors: Jean P. F. Van Wauwe, Beerse; Jan Heeres, Vosselaar; Leo J. J. Backx, Arendonk, all of Belgium

[73] Assignee: Janssen Pharmaceutica N.V., Beerse, Belgium

[21] Appl. No.: 297,010

[22] Filed: Jan. 12, 1989

Related U.S. Application Data

[63] Continuation-in-part of Ser. No. 161,825, Feb. 29, 1980, abandoned.

[51] Int. Cl.$^5$ ............ A61K 31/495; C07D 403/10; C07D 413/10; C07D 417/10
[52] U.S. Cl. ............................ 514/252; 514/227.2; 514/228.8; 514/241; 514/242; 514/255; 544/55; 544/96; 544/182; 544/219; 544/220; 544/230; 544/295; 544/366; 544/367; 544/369; 544/370; 544/371; 544/372; 544/392; 544/393
[58] Field of Search ............... 544/8.66, 96, 55, 182, 544/295, 366, 367, 370, 372, 392, 393, 394, 368, 218, 219, 230, 220, 369, 371; 514/252, 255, 227.2, 228.8, 241, 242

[56] References Cited

U.S. PATENT DOCUMENTS

| | | | |
|---|---|---|---|
| 3,720,690 | 3/1973 | King et al. | 544/376 |
| 4,144,346 | 3/1979 | Heeres et al. | 514/252 |
| 4,267,179 | 5/1981 | Heeres et al. | 514/252 |
| 4,335,125 | 6/1982 | Heeres et al. | 514/252 |
| 4,368,200 | 1/1983 | Heeres et al. | 514/252 |
| 4,503,055 | 3/1985 | Heeres et al. | 514/285 |
| 4,619,931 | 10/1986 | Heeres et al. | 514/252 |

FOREIGN PATENT DOCUMENTS 0228125 7/1987 European Pat. Off. .

OTHER PUBLICATIONS

King et al., Chemical Abstracts 79-32066y (1973).
Kiyoura et al., Chemical Abstracts 87-102378t (1977).

Primary Examiner—Cecilia Shen
Attorney, Agent, or Firm—Charles J. Metz

[57] ABSTRACT

4-(4-phenyl-1-piperazinyl)phenols for use as 5-lipoxygenase inhibitors and a method of treating warm-blooded animals suffering from leukotriene mediated diseases and disorders using the same. Pharmaceutical compositions containing the same as active ingredient. Novel compounds used in said method and processes for preparing said novel compounds.

12 Claims, No Drawings

5-LIPOXYGENASE INHIBITING 4-(4-PHENYL-1-PIPERAZINYL)PHENOLS

CROSS-REFERENCE TO RELATED APPLICATIONS

This application is a continuation-in-part of our co-pending application Ser. No. 161,825, filed Feb. 29, 1988, now abandoned.

BACKGROUND OF THE INVENTION

A number of 4-(4-phenyl-1-piperazinyl)phenyl derivatives are known from U.S. Pat. Nos. 4,267,179 and 4,619,931 and from EP-A-0,228,125 as intermediates for the preparation of compounds having antifungal and antibacterial properties. Additionally, the compound N,N'-bis(4-hydroxyphenyl)piperazine is known from U.S. Pat. No. 3,720,690, as an intermediate for the preparation of a compound useful in the treatment of allergic and autoimmune diseases.

DESCRIPTION OF THE INVENTION

The present invention is concerned with 5-lipoxygenase inhibiting 4-(4-phenyl-1-piperazinyl)phenyl derivatives having the formula

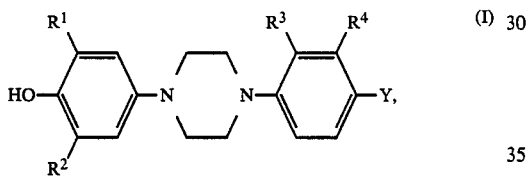

(I)

the pharmaceutically acceptable acid addition salts thereof, and the stereochemically isomeric forms thereof, wherein $R^1$ and $R^2$ each independently are hydrogen, $C_{1-6}$alkyl or halo;

$R^3$ and $R^4$ each independently are hydrogen, halo, amino, nitro or trifluoromethyl;

Y is hydrogen, nitro, amino, mono- or di($C_{1-6}$alkyl)amino, $C_{1-6}$alkylcarbonylamino, $C_{1-6}$alkyl, $C_{1-6}$alkylcarbonyl, hydroxy, halo, mono- or di-($C_{1-6}$alkyl)aminosulfonyl or a heterocyclic radical of formula

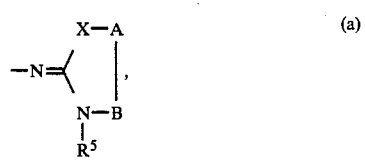  (a)

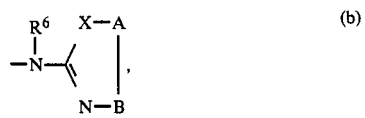  (b)

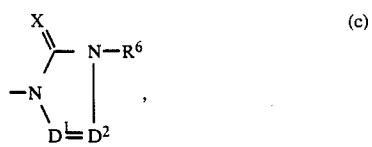  (c)

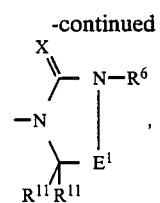  (d)

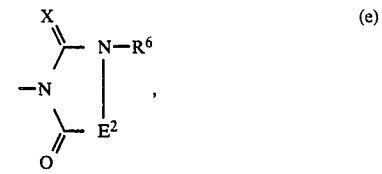  (e)

  (f)

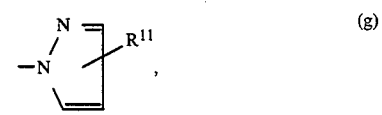  (g)

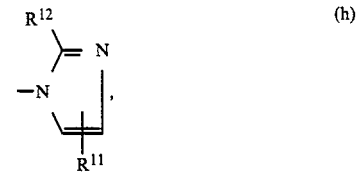  (h)

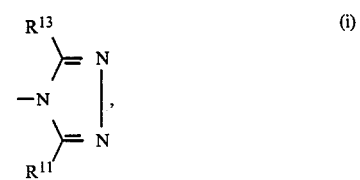  (i)

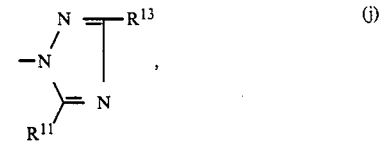  (j)

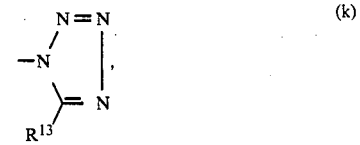  (k)

X is oxygen or sulfur;

$R^5$ and $R^6$ each independently are $C_{1-6}$alkyl, $C_{3-6}$alkenyl, $C_{3-6}$alkynyl, aryl, (aryl)$C_{1-6}$alkyl, $C_{3-7}$cycloalkyl, ($C_{3-7}$cycloalkyl)$C_{1-6}$alkyl, $C_{1-6}$alkyloxy$C_{1-6}$alkyl, mono-, di or trihalo$C_{1-6}$alkyl; said $C_{1-6}$alkyl, $C_{3-7}$cycloalkyl, ($C_{3-7}$cycloalkyl)$C_{1-6}$alkyl and (aryl)-$C_{1-6}$alkyl being optionally substituted with oxo or hydroxy on any carbon atom of the $C_{1-6}$alkyl or $C_{3-7}$cycloalkyl moiety, provided that said carbon atom is not adjacent to the nitrogen atom bearing said $R^5$ or $R^6$ radical; and $R^6$ may also be hydrogen;

A is —C($R^7$)($R^8$)— and B is —CH$_2$— or —CH$_2$—CH$_2$—, or A and B taken together form a bivalent radical of formula —CH=CH— (l) or —CH=N— (m), wherein the carbon atom of said radical is connected to X;

$R^7$ and $R^8$ each independently are hydrogen or $C_{1-6}$alkyl and $R^7$ may also be $C_{1-6}$alkyloxy; and in each of the bivalent radicals —B—, —CH=CH— (l) and —CH=N— (m) one or where possible two hydrogen atoms may be replaced by $C_{1-6}$alkyl or aryl; and in the bivalent radical B, two geminal hydrogen atoms may also be replaced by $C_{4-6}$alkanediyl optionally substituted with one or two $C_{1-6}$alkyl radicals;

$D^1$ is —N= or —CH=; and
$D^2$ is =N—, =CH— or =CH—C(=O)—;
$E^1$ is —CH$_2$—, —CH$_2$—CH$_2$— or —C(=O)—;
$E^2$ is —C($R^9$)($R^{10}$)— or —N$R^{11}$—C(=O)— wherein the carbonyl of said radical is connected to N$R^6$;

$R^9$ and $R^{10}$ are each independently hydrogen or $C_{1-6}$alkyl; or $R^9$ and $R^{10}$ taken together may form a bivalent $C_{4-6}$alkanediyl radical optionally substituted with one or two $C_{1-6}$alkyl radicals; or $R^6$ and $R^9$ taken together may form a bivalent $C_{3-5}$alkanediyl radical optionally substituted with one or two $C_{1-6}$alkyl radicals; and in each of the bivalent radicals $D^1$, $D^2$ and $E^1$, one or where possible two hydrogen atoms may be replaced by $C_{1-6}$alkyl;

each $R^{11}$ independently is hydrogen or $C_{1-6}$alkyl;
$R^{12}$ is hydrogen, $C_{1-6}$alkyl or $C_{1-6}$alkylthio;
$R^{13}$ is hydrogen or $C_{1-6}$alkylthio; and
aryl is phenyl optionally substituted with one to three radicals independently selected from halo, $C_{1-6}$alkyl, $C_{1-6}$alkyloxy, hydroxy or mono-, di- or trihalo$C_{1-6}$alkyl.

The radicals of formula (b), (c), (d) and (e), wherein $R^6$ is hydrogen may also exist in their tautomeric forms. Such forms, although not explicitly indicated in the above radicals (b), (c), (d) and (e), are intended to be included within the scope of formula (I).

As used in the foregoing definitions $C_{1-6}$alkyl denotes straight or branch chained saturated hydrocarbon radicals having from 1 to 6 carbon atoms, e.g. methyl, ethyl, propyl, 1-methylethyl, the four butyl isomers, the pentyl and hexyl isomers; $C_{3-6}$alkenyl defines straight and branch chained hydrocarbon radicals containing one double bond and having from 3 to 6 carbon atoms such as, for example, 2-propenyl, 2-butenyl, 3-butenyl, 2-methyl-2-propenyl, 2-pentenyl, 3-pentenyl, 4-pentenyl, 3-methyl-2-butenyl and the hexenyl isomers; $C_{3-6}$alkynyl defines straight and branch chained hydrocarbon radicals containing one triple bond and having from 3 to 6 carbon atoms such as, for example, 2-propynyl, 2-butynyl, 3-butynyl, 2-pentynyl, 3-pentynyl or 4-pentynyl and the hexynyl isomers; and when said $C_{3-6}$alkenyl or $C_{3-6}$alkynyl are substituted on a nitrogen atom, then the carbon atom of said $C_{3-6}$alkenyl or $C_{3-6}$alkynyl connected to said heteroatom preferably is saturated; $C_{3-7}$cycloalkyl defines cyclopropyl, cyclobutyl, cyclopentyl, cyclohexyl and cycloheptyl; $C_{3-5}$alkanediyl and $C_{4-6}$alkanediyl define bivalent saturated hydrocarbon radicals having from 3 to 5, respectively from 4 to 6 carbon atoms, e.g., 1,3-propanediyl, 1,4-butanediyl, 1,5-pentanediyl and 1,6-hexanediyl; halo is fluoro, chloro, bromo or iodo; the term mono-, di- and trihalo$C_{1-6}$alkyl as used hereinabove defines $C_{1-6}$alkyl radicals wherein one, two or three hydrogen atoms are replaced by halo atoms. Examples of such radicals are fluoromethyl, difluoromethyl, trifluoromethyl, trichloromethyl, 2-chloroethyl, 2,2,2-trifluoroethyl and the like.

Depending on the nature of the various substituents the compounds of formula (I) may contain asymmetrical carbon atoms. Unless otherwise mentioned or indicated, the chemical designation of compounds denotes the mixture of all possible stereochemically isomeric forms, said mixtures containing all diastereoisomers and enantiomers of the basic molecular structure. The absolute configuration of each chiral center may be indicated by the stereochemical descriptors R and S, this R and S notation corresponding to the rules described in Pure Appl. Chem. 1976, 45, 11–30. In some compounds the stereochemical configuration is not experimentally determined. In those cases it is conventionally agreed to designate the stereochemically isomeric form which is first isolated as "A" and the second as "B", without further reference to the actual stereochemical configuration.

Pure isomeric forms of the compounds of formula (I) can be separated from the mixture by conventional separation methods. Preferably, if a specific stereoisomer is desired, said compound will be synthesized by stereoselective methods of preparation. These methods will advantageously employ enantiomerically pure starting materials.

The compounds of formula (I) have basic properties and, consequently, they may be converted to their therapeutically active non-toxic acid addition salt forms by treatment with appropriate acids such as, for example, inorganic acids, e.g. hydrochloric, hydrobromic and the like acids, sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The term acid addition salt as used hereinabove also comprises the solvates which the compounds of formula (I) are able to form and said solvates are meant to be included within the scope of the present invention. Examples of such solvates are e.g., the hydrates, alcoholates and the like.

A particular group among the compounds of formula (I) comprises those compounds of formula (I) wherein Y is a radical of formula (a), (b), (c), (d) or (e); and $R^5$, respectively $R^6$ is $C_{1-6}$alkyl, $C_{3-7}$cycloalkyl, (aryl)$C_{1-6}$alkyl all being optionally substituted with oxo or hydroxy on the $C_{1-6}$alkyl or $C_{3-7}$cycloalkyl moiety; or $R^5$, respectively $R^6$ is $C_{1-6}$alkyloxy$C_{1-6}$alkyl, mono-, di- or trihalo$C_{1-6}$alkyl.

A more particular group of compounds of formula (I) comprises those compounds of formula (I) wherein Y is a radical of formula (a), $R^5$ is $C_{1-6}$alkyl and A-B is CH=CH, (CH$_2$)$_3$ or C(CH$_3$)$_2$—CH$_2$;

Y is a radical of formula (b), $R^6$ is $C_{1-6}$alkyl and A-B is CH$_2$—CH$_2$ wherein one or two hydrogen atoms may be replaced by $C_{1-6}$alkyl or two geminal hydrogen atoms may be replaced by $C_{4-6}$alkanediyl;

Y is a radical of formula (c), X is O, $R^6$ is $C_{1-6}$alkyl, (aryl)$C_{1-6}$alkyl, $C_{3-7}$cycloalkyl, mono-, di- or trihaloC$_{1-6}$alkyl; said $C_{1-6}$alkyl, (aryl)$C_{1-6}$alkyl and $C_{3-7}$cycloalkyl being optionally substituted with oxo or hydroxy on the $C_{1-6}$alkyl or $C_{3-7}$cycloalkyl moiety; and $D^1=D^2$ is CH=N wherein hydrogen may be replaced by $C_{1-6}$alkyl;

Y is a radical of formula (d), X is O, $R^6$ is $C_{1-6}$alkyl or (aryl)$C_{1-6}$alkyl both being optionally substituted with oxo or hydroxy on the $C_{1-6}$alkyl moiety; and Y is a radical of formula (e) and $R^6$ is $C_{1-6}$alkyl or (aryl)$C_{1-6}$alkyl both being optionally substituted with oxo or hydroxy on the $C_{1-6}$alkyl moiety.

The most interesting compounds are 2,4-dihydro-4-[4-[4-(4-hydroxy-3,5-dimethylphenyl)-1-piperazinyl]phenyl]-5-methyl-2-(1-methylpropyl)-3H-1,2,4-triazol-3-one, 2,4-dihydro-4-[4-[4-(4-hydroxyphenyl)-1-piperazinyl]phenyl]-5-methyl-2-(1-methylpropyl)-3H-1,2,4-triazol-3-one, 2-[2-(4-bromophenyl)-1-methyl-2-oxoethyl]-2,4-dihydro-4-[4-[4-(4-hydroxy-3,5-dimethylphenyl)-1-piperazinyl]phenyl]-5-methyl-3H-1,2,4-triazol-3-one, 2-[2-(4-bromophenyl)-1-methyl-2-oxoethyl]-2,4-dihydro-4-[4-[4-(4-hydroxyphenyl)-1-piperazinyl]phenyl]-5-methyl-3H-1,2,4-triazol-3-one, 2-[2-(4-bromophenyl)-2-hydroxy-1-methylethyl]-2,4-dihydro-4-[4-[4-(4-hydroxyphenyl)-1-piperazinyl]phenyl]-5-methyl-3H-1,2,4-triazol-3-one, and 2-[2-(4-bromophenyl)-2-hydroxy-1-methylethyl]-2,4-dihydro-4-[4-[4-(4-hydroxy-3,5-dimethylphenyl)-1-piperazinyl]phenyl]-5-methyl-3H-1,2,4-triazol-3-one.

An additional feature of the present invention comprises the fact that a number of the compounds of formula (I) are novel and have especially been developed to be used as 5-lipoxygenase inhibitors in the method according to the present invention.

Novel compounds of formula (I), which hereinafter and in the claims will be referred to as compounds of formula (I-a), are those compounds of formula (I) wherein Y and $R^1$ to $R^{13}$ are as defined hereinabove and wherein at least one of $R^1$ or $R^2$ is $C_{1-6}$alkyl or halo; and/or at least one of $R^3$ or $R^4$ is halo, amino, nitro or trifluoromethyl; and/or Y is mono- or di($C_{1-6}$alkyl)amino, ($C_{1-6}$alkyl)carbonylamino, $C_{1-6}$alkyl, $C_{1-6}$alkylcarbonyl, halo, mono- or di($C_{1-6}$alkyl)aminosulfonyl, or a radical of formula

 (a-1)

 (a-2)

 (b)

 (c-1)

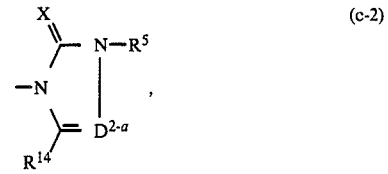 (c-2)

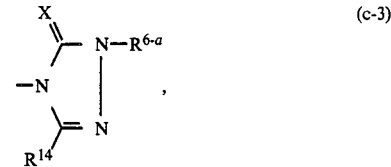 (c-3)

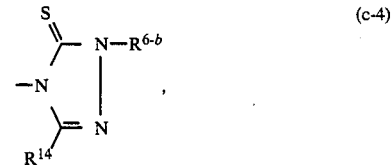 (c-4)

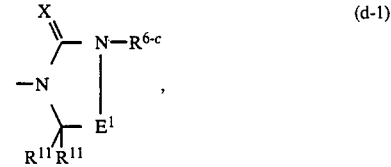 (d-1)

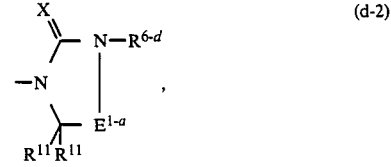 (d-2)

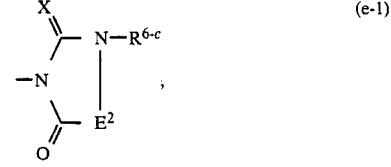 (e-1)

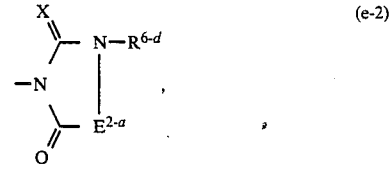 (e-2)

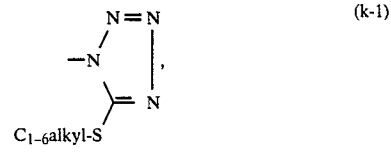 (k-1)

wherein X, $R^5$, $R^6$, A, B, $D^2$, $E^1$, $E^2$, $R^{11}$ and aryl are as defined under formula (I) and $R^{5-a}$ is mono, di- or trihalo$C_{1-6}$alkyl; $C_7$cycloalkyl or ($C_7$cycloalkyl)$C_{1-6}$alkyl, both being optionally substituted with oxo or hydroxy on the $C_{1-6}$alkyl or $C_7$cycloalkyl moiety;

$R^{5-b}$ is $C_{1-6}$alkyl, $C_{3-6}$cycloalkyl or ($C_{3-6}$cycloalkyl)-$C_{1-6}$alkyl or (aryl)$C_{1-6}$alkyl, all being substituted with oxo or hydroxy on the C$_{1-6}$alkyl or C$_{3-6}$cycloalkyl moiety;

B$^1$ is —CH$_2$—CH$_2$— wherein one or two hydrogen atoms may be replaced by C$_{1-6}$alkyl or aryl, or two geminal hydrogen atoms may be replaced by a C$_{4-6}$alkanediyl radical optionally substituted with one or two C$_{1-6}$alkyl radicals;

D$^{2-a}$ is =CH— or =CH—C(=O)— wherein the hydrogen atom may be replaced by C$_{1-6}$alkyl;

R$^{14}$ is hydrogen or C$_{1-6}$alkyl;

R$^{6-a}$ is C$_{3-6}$alkenyl, C$_{3-6}$alkynyl, aryl, C$_{3-7}$cycloalkyl, (C$_{3-7}$cycloalkyl)C$_{1-6}$alkyl, C$_{1-6}$alkyloxyC$_{1-6}$alkyl, mono-, di- or trihaloC$_{1-6}$alkyl; C$_7$cycloalkyl or (C$_7$cycloalkyl)C$_{1-6}$alkyl, both being substituted with oxo or hydroxy on the C$_{1-6}$alkyl or C$_7$cycloalkyl moiety;

R$^{6-b}$ is C$_{1-6}$alkyl, (aryl)C$_{1-6}$alkyl; or C$_{1-6}$alkyl, C$_{3-6}$cycloalkyl, (C$_{3-6}$cycloalkyl)-C$_{1-6}$alkyl and (aryl)C$_{1-6}$alkyl being substituted with oxo or hydroxy on the C$_{1-6}$alkyl or C$_{3-6}$cycloalkyl moiety;

R$^{6-c}$ is mono-, di- or trihaloC$_{1-6}$alkyl; C$_7$cycloalkyl or (C$_7$cycloalkyl)C$_{1-6}$alkyl, both being optionally substituted with oxo or hydroxy on the C$_{1-6}$alkyl or C$_7$cycloalkyl moiety; or R$^{6-c}$ and R$^9$ taken together may form a bivalent C$_{3-5}$alkanediyl radical optionally substituted with one or two C$_{1-6}$alkyl radicals;

E$^{1-a}$ is —CH$_2$—CH$_2$— wherein one or two hydrogen atoms may be replaced by C$_{1-6}$alkyl;

R$^{6-d}$ is hydrogen, C$_{3-6}$ alkenyl, C$^{3-6}$ alkynyl, aryl, cycloalkyl, (C$_{3-6}$cycloalkyl)-C$_{1-6}$alkyl, C$_{1-6}$alkyloxyC$_{1-6}$alkyl; or C$_{1-6}$alkyl, C$_{3-6}$cycloalkyl, (C$_{3-6}$cycloalkyl)-C$_{1-6}$alkyl or (aryl)C$_{1-6}$alkyl being substituted with oxo or hydroxy on the C$_{1-6}$alkyl or C$_{3-6}$cycloalkyl moiety; and E$^{2-a}$ is —NR$^{11}$—C(=O)—.

Particular novel compounds are those novel compounds as defined hereinabove wherein at least one of R$^1$ or R$^2$ is C$_{1-4}$alkyl or halo; and/or at least one of R$^3$ or R$^4$ is halo, amino, nitro or trifluoromethyl; and/or Y is a radical of formula

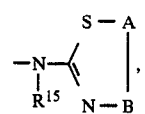 (b-1)

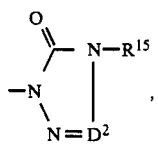 (c-1a)

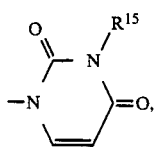 (c-2a)

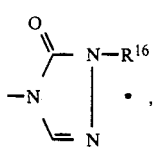 (c-3a)

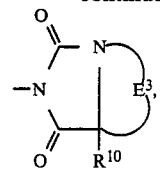 (e-1a)

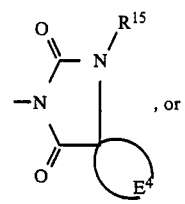 (e-1b)

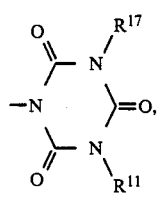 (e-2a)

wherein A, B, D$^2$, R$^{10}$ and R$^{11}$ are as defined hereinabove and

R$^{15}$ is C$_{1-6}$alkyl;

R$^{16}$ is mono-, di- or trihaloC$_{1-6}$alkyl; C$_{3-6}$cycloalkyl; or C$_7$ cycloalkyl optionally substituted with oxo;

E$^3$ is C$_{3-5}$alkanediyl;

E$^4$ is C$_{4-6}$alkanediyl;

R$^{17}$ is (aryl)C$_{1-6}$alkyl substituted with oxo or hydroxy on the C$_{1-6}$alkyl moiety.

More particular novel compounds are those particular novel compounds as defined hereinabove wherein at least one of R$^1$ or R$^2$ is methyl and/or Y is a radical of formula (c-3a), (e-1a) or (e-2a).

The most interesting novel compounds are 2,4-dihydro-4-[4-[4-(4-hydroxy-3,5-dimethylphenyl)-1-piperazinyl]phenyl]-5-methyl-2-(1-methylpropyl)-3H-1,2,4-triazol-3-one, 2-[2-(4-bromophenyl)-1-methyl-2-oxoethyl]-2,4-dihydro-4-[4-[4-(4-hydroxy-3,5-dimethylphenyl)-1-piperazinyl]phenyl]-5-methyl-3H-1,2,4-triazol-3-one and 2-[2-(4-bromophenyl)-2-hydroxy-1-methylethyl]-2,4-dihydro-4-[4-[4-(4-hydroxy-3,5-dimethylphenyl)-1-piperazinyl]phenyl]-5-methyl-3H-1,2,4-triazol-3-one.

Procedures for the preparation of a number of the compounds of formula (I) have been described in U.S. Pat. Nos. 4,267,179 and 4,619,931 and in EP-A-0,228,125.

Novel compounds of formula (I-a) as defined hereinabove can generally be prepared following said or alternative procedures or, in some instances, following optimized modifications thereof. A number of such procedures will be described hereinafter in some more detail. The compounds of formula (I) can generally be obtained from alkyloxy-derivatives of formula (II) by an appropriate dealkylation reaction, e.g. in an acidic medium using a strong non-oxidizing acid, e.g. trifluoroacetic acid, boron tribromide or a mineral acid such as concentrated hydrohalic acid e.g. hydrobromic acid, hydroiodic acid, optionally in admixture with a saturated solution of hydrobromic acid in glacial acetic acid; or with a strong nucleophile such as an alcoholate or a thiolate, e.g. lithium isopropylthiolate.

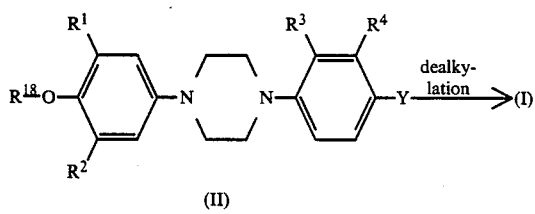

(II) $R^{18}$ represents an alkyl, in particular a $C_{1-6}$alkyl group and preferably a methyl group. In the instance where hydrobromic acid is used it may be advantageous to conduct said dealkylation reaction in the presence of a bromine scavenger such as, for example sodium sulfite or hydrogen sulfite.

The compounds of formula (I) can also be prepared by N-arylating a piperazine of formula (III) with a substituted benzene of formula (IV) wherein W is an appropriate leaving group, in particular halo, and preferably is fluoro or chloro.

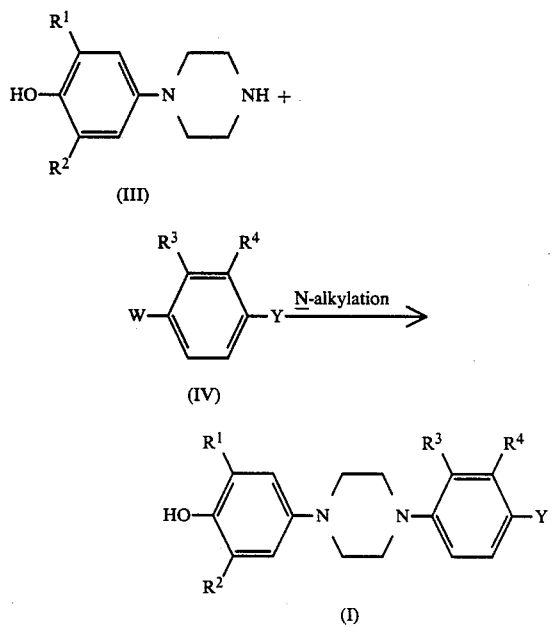

Said N-arylation reaction can be carried out according to art-known procedures, e.g. by stirring the reactants, preferably at a somewhat elevated temperature in an appropriate solvent such as dipolar aprotic solvent, for example, dimethylsulfoxide, N,N-dimethylformamide, N,N-dimethylacetamide; an alcohol, e.g. 1-butanol, an ether, e.g. tetrahydrofuran and the like solvents. In particular, the reaction may be conducted in the presence of an appropriate base such as, for example, an alkali metal hydride or carbonate.

The compounds of formula (I) can also be converted into each other following art-known procedures of functional group transformation. Some examples will be cited hereinafter.

The compounds of formula (I) having a nitro substituent can be converted into the corresponding amines by stirring and, if desired, heating the starting nitro-compounds in a hydrogen-containing medium in the presence of a suitable amount of an appropriate catalyst such as, for example, platinum-on-charcoal, palladium-on-charcoal, Raney-nickel and the like catalysts. Suitable solvents are, for example, alcohols, e.g., methanol, ethanol and the like.

Halo atoms substituted on aryl groups may be replaced by hydrogen following art-known hydrogenolysis procedures, i.e. by stirring and, if desired, heating the starting compounds in a suitable solvent under hydrogen atmosphere in the presence of an appropriate catalyst, e.g., palladium-on-charcoal and the like catalysts.

The compounds of formula (I) wherein Y is amino can also be converted into other compounds encompassed by formula (I); e.g. the compounds wherein Y is $(C_{1-6}alkyl)$carbonylamino can be obtained by a selective N-acylation reaction with an carboxylic acid halogenide or anhydride in a suitable solvent such as, for example an aromatic hydrocarbon, e.g. benzene, methylbenzene and the like, a dipolar aprotic solvent, e.g. N,N-dimethylformamide, dimethyl sulfoxide and the like, or a mixture of such solvents, and in the presence of an appropriate base, e.g. N,N-diethylethanamine, pyridine and the like bases.

A number of intermediates and starting materials in the foregoing preparations are known compounds which may be prepared according to art-known methodologies of preparing said or similar compounds and some intermediates are new. A number of such preparation methods will be described hereinafter in more detail.

In order to simplify the structural representations of some of the intermediates in the following preparations, the 4-(4-phenyl-1-piperazinyl)alkyloxyphenyl group wherein $R^1$, $R^2$, $R^3$ and $R^4$ are as defined under formula (I), will hereinafter be represented by the symbol T.

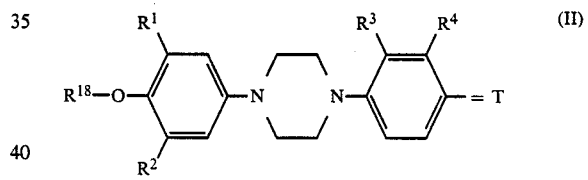

For example, the intermediates of formula (II), wherein Y is a heterocycle of formula (b) and -A-B- is a radical of formula $-C(R^{19})=C(R^{20})-$, said $R^{19}$ and $R^{20}$ independently being hydrogen, $C_{1-6}$alkyl or aryl, and said intermediates being represented by formula (II-a), may be prepared by condensing a thiourea (X=S) or urea (X=O) of formula (V) with an appropriate α-halo-ketone of formula (VI), in an acidic buffer such as a carboxylic acid, e.g. acetic acid and the like, in the presence of an alkali metal salt of said carboxylic acid, at an elevated temperature. In formula (VI), $W^1$ represents halo, preferably chloro or bromo. The intermediates of formula (II-a) may be alkylated with a reagent $R^{6-a}$—W, wherein $R^{6-a}$ is as $R^6$, provided it is not hydrogen, and W is a reactive leaving group.

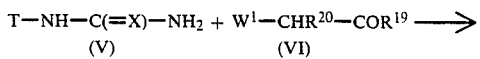

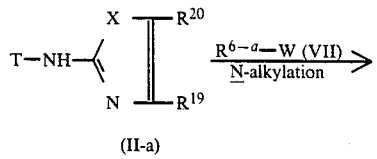

-continued

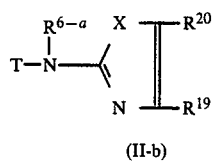

The intermediates of formula (II), wherein Y is a heterocycle of formula (b) wherein -A- is a radical —CH(OC$_{1-6}$alkyl)—; and R$^6$ is other than hydrogen, said intermediates being represented by formula (II-c), can be obtained by reacting an amine of formula (VIII) with an isothiocyanate (X=S) or isocyanate (X=O) of formula (IX)

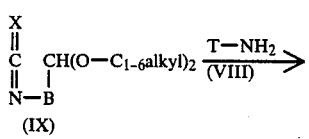

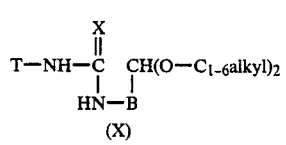

and subsequently cyclizing the acetal (X) in an acidic solvent such as a carboxylic acid, e.g. formic acid, thus obtaining an intermediate (II-d) which may be alkylated to an intermediate (II-c) with a suitable alkylating reagent R$^{6-a}$—W (VII), following the same procedure as described above for the preparation of (II-b).

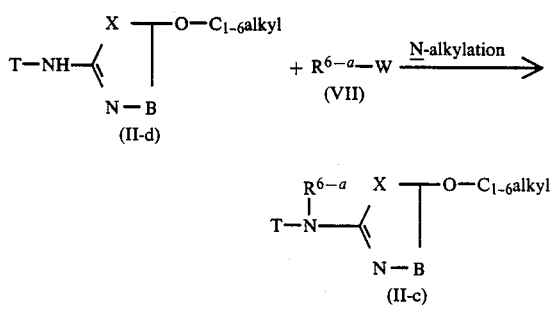

The intermediates of formula (II) wherein A-B is C(R$^{21}$)=N, said R$^{21}$ being hydrogen or C$_{1-6}$alkyl and said intermediates being represented by formula (II-e), can be prepared by reacting a hydrazine carbothiamide (X=S) or hydrazine carboxamide (X=O) of formula (XI) with an appropriate acylating reagent, e.g. an acyl halide (Z=halo) or anhydride (Z=RCOO) of formula (XII) in a reaction-inert solvent at an elevated temperature; and then treating the thus obtained intermediate (XIII) with a suitable acid such as a sulfonic acid, e.g. methanesulfonic acid, optionally in a reaction-inert solvent.

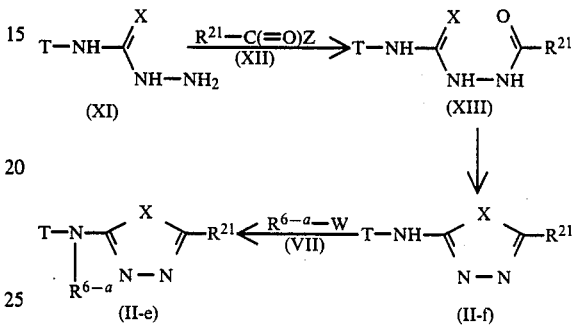

The intermediate of formula (II-f) further may be alkylated to an intermediate (II-e) with an alkylating reagent R$^{6-a}$—W (VII) following the same procedure as described above for the preparation of (II-b).

The intermediates of formula (II) wherein Y is a heterocycle of formula (c) and D$^1$=D$^2$ is N=CR$^{24}$, said R$^{24}$ being hydrogen or C$_{1-6}$alkyl and said intermediates being represented by formula (II-g), may be obtained as follows. An appropriate 4-nitrophenylhydrazine (XIV) is reacted with an iminoether of formula (XV), followed by a substitution reaction with a secondary amine R$^{22}$R$^{23}$NH (XVI), wherein R$^{22}$ and R$^{23}$ are C$_{1-6}$alkyl or R$^{22}$ and R$^{23}$ complete a pyrrolidinyl, piperidinyl or morpholinyl ring. The thus obtained hydrazine derivative (XVII) is subsequently cyclized with an isocyanate (XVIII) to yield a 4-nitrophenyltriazolone (XIX), which in turn is reduced to a 4-aminophenyltriazolone (XX). The latter is subsequently condensed with a 4-methoxyaniline of formula (XXI) thus yielding the desired intermediates of formula (II-g).

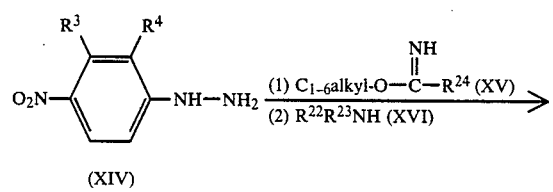

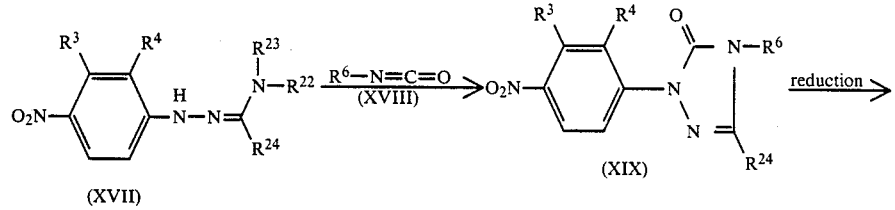

-continued

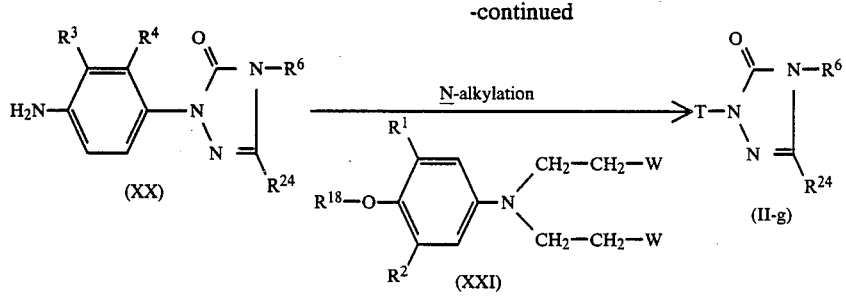

The intermediates of formula (II), wherein Y is a heterocycle of formula (c) and $D^1=D^2$ is $CR^{24}=N$, said $R^{24}$ being hydrogen or $C_{1-6}$alkyl and said intermediates being represented by formula (II-h), may also be obtained by cyclizing an amine (VIII) with aminomethylene hydrazine carboxylate derivative (XXII) preferably in a high-boiling aprotic solvent such as tetrahydrothiophene 1,1-dioxide and N-alkylating the thus obtained intermediate (XXV) with a reagent $R^{6-a}$—W (VII), following the same procedure as described above for the preparation of (II-b).

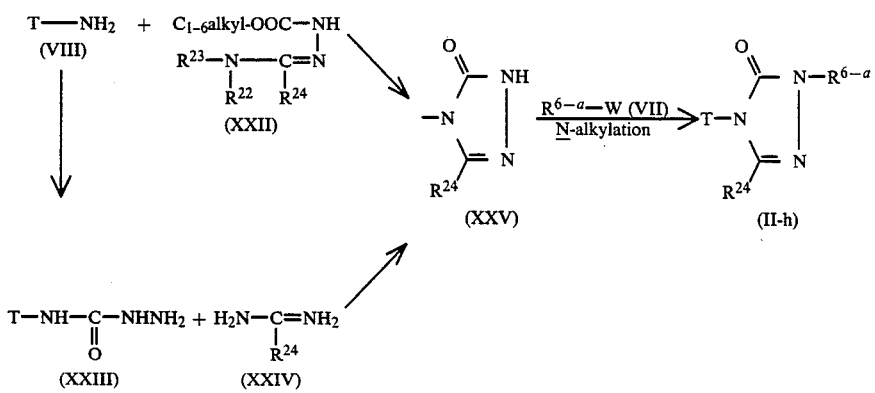

Alternatively, treatment of the amine (VIII) with a carbonochloridate, e.g. phenyl carbonochloridate, followed by a substitution reaction with hydrazine, yields the hydrazine carboxamide (XXIII), which can easily be cyclized to an intermediate of formula (XXV) upon treatment with an amidine (XXIV) or a corresponding salt form thereof.

Pure stereochemically isomeric forms of the compounds of formula (I) may be obtained by the application of art-known procedures. Diastereoisomers may be separated by physical separation methods such as selective crystallization and chromatographic techniques, e.g. counter current distribution, column chromatography or high performance liquid chromatography, and enantiomers may be separated according to art-known resolution methods, e.g. by the selective crystallization of the diastereomeric salts obtained with optically active acids. Pure stereochemically isomeric forms may also be prepared from the corresponding pure stereochemically isomeric forms of the appropriate starting materials by stereospecific reactions.

The compounds of formula (I) are potent and selective inhibitors of the 5-lipoxygenase enzyme both in vitro and in vivo. Inhibition of the 5-lipoxygenase enzyme effectively blocks the metabolic pathway leading from arachidonic acid to leukotrienes, which substances are known to possess a range of potent physiological effects and are presumed to be involved in a variety of allergic, anaphylactic and inflammatory reactions (Science, 220, 568–575, 1983).

Leukotrienes $C_4$, $D_4$ and $E_4$ ($LTC_4$, $LTD_4$ and $LTE_4$) strongly induce the contraction of smooth muscles and in particular exhibit powerful bronchoconstricting properties. Further, said leukotrienes increase the vascular permeability, thus resulting in the leakage of intravascular fluid and proteins into the tissues and the formation of edema. Leukotriene $B_4$, a potent chemokinetic and chemotactic agent towards leukocytes, has been proposed as an important mediator in immediate and subacute hypersensitivity reactions and inflammatory processes (The New England Journal of Medicine, 303, 822–825, 1980; "The Leukotrienes: Chemistry and Biology", ed. L. W. Chakrin, D. M. Bailey, Academic Press, Orlando, 195–214, 1984). The above-mentioned leukotrienes are all derived from a common intermediate, 5-hydroperoxyeicosatetraenoic acid (5-HPETE) which is formed from arachidonic acid through the activity of a 5-lipoxygenase. Other lipoxygenases, e.g. 12- and 15-lipoxygenase, transform arachidonic acid into several other mono- and dihydroxy derivatives with opposite or synergistic biological activities. Additionally, an increased release of the products of 5-lipoxygenase and 12-lipoxygenase enzymatic activity from the lesioned skin of patients with psoriasis as well as with atopical dermatitis has been reported (Prostaglandins 29, 611–619, 1985; J. Invest. Dermatol. 83, 70–73, 1983; Lancet, i, 222–223, 1984).

Consequently, inhibitors of the lipoxygenase-mediated metabolic pathways of arachidonic acid, and in particular of the 5-lipoxygenase enzyme, are considered to be valuable therapeutical drugs for suppressing the abovementioned adverse effects of leukotrienes. Associated diseases and/or disorders are, for instance, asthma, allergy, anaphylaxis, psoriasis and inflammatory reactions, e.g. arthritis and dermatitis. The invention gains importance by the fact that the compounds of formula (I) to be used in the present method are both potent and selective inhibitors towards the 5-lipoxygenase enzyme. Most other inhibitors reported lack selectivity and concomitantly inhibit other lipoxygenases and/or cyclooxygenase, the enzyme which mediates the metabolism of arachidonic acid towards the prostaglandines. The compounds of formula (I) do not significantly inhibit soy bean 15-lipoxygenase, human platelet 12-lipoxygenase, human platelet cyclooxygenase nor thromboxane $A_2$ synthetase. Furthermore, the compounds of formula (I) generally show only moderate non-specific anti-oxidant properties.

Another important feature of the present invention is the fact that the compounds of formula (I) are orally active as is shown in the "Inhibition of Dextran-induced edema formation in the ears of mice" test (Example 23).

The present invention also relates to a method of treating warm-blooded animals suffering from leukotriene-mediated diseases and/or disorders, by administering an effective 5-lipoxygenase inhibiting amount of a compound of formula (I) or a pharmaceutically acceptable acid addition salt thereof. Those of skill in the relevant art could easily determine the effective amount of 5-lipoxygenase inhibitor from the results presented hereinafter. In general it is contemplated that a suitable dose administered daily to subjects would be from about 0.1 mg/kg to about 50 mg/kg body weight, and more preferably from about 1 mg/kg to about 10 mg/kg body weight.

In view of their 5-lipoxygenase inhibiting activity, the subject compounds may be formulated into various pharmaceutical forms for administration purposes. To prepare the pharmaceutical compositions of this invention, an effective amount of the particular compound or an acid addition salt thereof, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoon-fuls and the like, and segregated multiples thereof.

The following examples are intended to illustrate and not to limit the scope of the present invention in all its aspects. Unless otherwise stated all parts therein are by weight.

EXPERIMENTAL PART

A. Preparation of Intermediates

Example 1

(a) To a stirred solution of 20 parts of 1-(4-isothiocyanatophenyl)-4-(4-methoxyphenyl)piperazine in 325 parts of dichloromethane were added 40 parts of methanol, saturated with ammonia. The reaction mixture was stirred for 5 days at room temperature. The precipitated product was filtered off, washed with dichloromethane and dried, yielding 20.5 parts (98.1%) of N-[4-[4-(4-methoxyphenyl)-1-piperazinyl]phenyl]thiourea; mp. 265.2° C. (int. 1).

(b) A mixture of 5 parts of N-[4-[4-(4-methoxyphenyl)-1-piperazinyl]phenyl]thiourea, 3 parts of 2-chloro-1-phenylethanone, 1.7 parts of sodium acetate and 100 parts of acetic acid was stirred for 4 hours at 80° C. After cooling, the reaction mixture was evaporated and the residue was stirred in 130 parts of dichloromethane. The whole was neutralised with a sodium hydrogen carbonate solution. The precipitated product was filtered off, washed with water and dichloromethane and crystallized from 1,4-dioxane. The product was filtered off and dried, yielding 4.5 parts (69.6%) of N-[4-[4-(4-methoxyphenyl)-1-piperazinyl]phenyl]-4-phenyl-2-thiazolamine; mp. 269.7° C. (int. 2).

(c) A mixture of 4.6 parts of N-[4-[4-(4-methoxyphenyl)-1-piperazinyl]phenyl]-4-phenyl-2-thiazolamine, 2 parts of bromoethane, 1 part of sodium hydroxide and 94 parts of N,N-dimethylformamide was stirred for 16 hours at room temperature. Another portion of 2 parts of bromoethane and 1 part of sodium hydroxide was added and stirring was continued for 4 hours at 50° C. The reaction mixture was diluted with water. The precipitated product was filtered off and purified by column chromatography over silica gel using trichloromethane as eluent. The pure fractions were collected and the eluent was evaporated. The residue was crystallized from 4-methyl-2-pentanone. The product was filtered off and dried, yielding 4.0 parts (81.7%) of N- ethyl-N-[4-[4-(4-methoxyphenyl)-1-piperazinyl]-phenyl]-4-phenyl-2-thiazolamine; mp. 223.6° C. (int. 3).

Example 2

(a) A mixture of 5.7 parts of 4-[4-(4-methoxyphenyl)-1-piperazinyl]benzenamine, 3 parts of 2-isothiocyanato-1,1-methoxyethane and 100 parts of 1,4-dioxane was stirred and refluxed for 1 hour. The reaction mixture was evaporated. The residue was purified by column chromatography over silica gel using a mixture of trichloromethane and methanol (98:2 by volume) as eluent. The pure fractions were collected and the eluent was evaporated. The residue was crystallized from 4-methyl-2-pentanone, yielding 3.1 parts (36%) of N-(2,2-dimethoxyethyl)-N'-[4-[4-(4-methoxyphenyl)-1-piperazinyl]phenyl]thiourea (int. 4).

(b) A mixture of 17.6 parts of N-(2,2-dimethoxyethyl)-N'-[4-[4-(4-methoxyphenyl)-1-piperazinyl]-phenyl]thiourea and 120 parts of formic acid was stirred for 1 hour at room temperature. The reaction mixture was evaporated in vacuo and the residue was dissolved in 133 parts of dichloromethane. The mixture was neutralized with a sodium hydrogen carbonate solution. The precipitated product was filtered off, washed with water and dichloromethane and crystallized from 4-methyl-2-pentanone. The product was filtered off and dried, yielding 8.5 parts (52.0%) of 4,5-dihydro-5-methoxy-N-[4-[4-(4-methoxyphenyl)-1-piperazinyl]-phenyl]-2-thiazolamine; mp. 177.5° C. (int. 5).

(c) A mixture of 15 parts of 4,5-dihydro-5-methoxy-N-[4-[4-(4-methoxyphenyl)-1-piperazinyl]phenyl]-2-thiazolamine, 5.8 parts of bromoethane, 3 parts of sodium hydroxide pellets and 207 parts of N,N-dimethylformamide was stirred for 16 hours at room temperature. The reaction mixture was diluted with water. The precipitated product was filtered off and purified by column chromatography over silica gel using a mixture of trichloromethane, ethyl acetate, hexane and methanol (49::30:20:1 by volume) as eluent. The second fraction was collected and the eluent was evaporated. The residue was crystallized from 4-methyl-2-pentanone. The product was filtered off and dried, yielding 7.3 parts (44.4%) of N-ethyl-4,5-dihydro-5-methoxy-N-[4-[4-(4-methoxyphenyl)-1-piperazinyl]phenyl]-2-thiazolamine hemihydrate; mp. 131.5° C. (int. 6).

Example 3

(a) A mixture of 10 parts of 1-(4-isothiocyanatophenyl)-4-(4-methoxyphenyl)piperazine, 3 parts of 2-amino-2-methyl-1-propanol and 260 parts of dichloromethane was stirred overnight at room temperature. The precipitated product was filtered off, washed with dichloromethane and 2-propanone and dried, yielding 11.7 parts (91.9%) of N-(2-hydroxy-1,1-dimethylethyl)-N'-[4-[4-(4-methoxyphenyl)-1-piperazinyl]phenyl]thiourea; mp. 221.6° C. (int. 7).

(b) A mixture of 74 parts of N-(2-hydroxy-1,1-dimethylethyl)-N'-[4-[4-(4-methoxyphenyl)-1-piperazinyl]-phenyl]thiourea and 360 parts of formic acid was stirred for 4 hours at 70° C. The reaction mixture was evaporated and the residue was dissolved in 260 parts of dichloromethane. The whole was neutralized with a sodium hydrogen carbonate solution. The precipitated product was filtered off, washed with water and dichloromethane and purified by column chromatography over silica gel using a mixture of trichloromethane and methanol, saturated with ammonia, (99:1 by volume) as eluent. The pure fractions were collected and the eluent was evaporated. The residue was crystallized from 4-methyl-2-pentanone. The product was filtered off and dried, yielding 44.1 parts (62.4%) of 4,5-dihydro-N-[4-[4-(4-methoxyphenyl)-1-piperazinyl]phenyl]-4,4-dimethyl-2-thiazolamine; mp. 232.0° C. (int. 8).

(c) A mixture of 37 parts of 4,5-dihydro-N-[4-[4-(4-methoxyphenyl)-1-piperazinyl]phenyl]-4,4-dimethyl-2-thiazolamine, 5 parts of a sodium hydride dispersion 50% and 376 parts of N,N-dimethylformamide was stirred for 2 hours at 70° C. After cooling to room temperature, 14.1 parts of iodomethane were added slowly to the reaction mixture. The whole was stirred for 1 hour at room temperature. The reaction mixture was diluted with water. The precipitated product was filtered off, washed with water and 2-propanol and purified by column chromatography (HPLC) over silica gel using a mixture of dichloromethane and methanol (96:4 by volume) as eluent. The first fraction was collected and the eluent was evaporated. The residue was further purified by column chromatography over silica gel using a mixture of dichloromethane and methanol (98:2 by volume). The pure fractions were collected and the eluent was evaporated. The residue was crystallized from 4-methyl-2-pentanone, yielding 4-[4-(4-methoxyphenyl)-1-piperazinyl]-N-(3,4,4-trimethyl-2-thiazolidinylidene)-benzenamine (int. 9). The second fraction was collected and boiled in 2-propanol. After cooling, the product was filtered off and dried, yielding 19.5 parts (51.0%) of 4,5-dihydro-N-[4-[4-(4-methoxyphenyl)-1-piperazinyl]phenyl]-N,4,4-trimethyl-2-thiazolamine; mp. 166.6° C. (int. 10)

Example 4

(a) A mixture of 47.8 parts of 1-(4-isothiocyanatophenyl)-4-(4-methoxyphenyl)piperazine, 100 parts of hydrazine hydrate and 400 parts of 1,4-dioxane was stirred and refluxed for 1 hour. The reaction mixture was cooled and poured into water. The precipitated product was filtered off, washed with water and methanol and dried, yielding 46 parts (89%) of N-[4-[4-(4-methoxyphenyl)-1-piperazinyl]phenyl]hydrazinecarbothioamide (int. 11).

(b) A mixture of 3.6 parts of N-[4-[4-(4-methoxyphenyl)-1-piperazinyl]phenyl]hydrazinecarbothioamide, 1 part of acetic acid anhydride and 150 parts of trichloromethane was stirred for 1 hour at reflux temperature. After cooling, the precipitated product was filtered off and dried, yielding 3.6 parts (90.1%) of acetic acid, 2-[[[4-[4-(4-methoxyphenyl)-1-piperazinyl]phenyl]amino]thioxomethylhydrazide; mp. 229.8° C. (int. 12).

(c) A mixture of 2.6 parts of acetic acid, 2-[[[4-[4-(4-methoxyphenyl)-1-piperazinyl]phenyl]amino]thioxomethylhydrazide and 74 parts of methanesulfonic acid was stirred for 2 hours at room temperature. The reaction mixture was poured into a mixture of ammonium hydroxide in crushed ice while stirring. The precipitated product was filtered off, washed with water and crystallized from N,N-dimethylformamide. The product was filtered off and dried, yielding 2.1 parts (84.7%) of N-[4-[4-(4-methoxyphenyl)-1-piperazinyl]phenyl]-5-methyl-1,3,4-thiadiazol-2-amine; mp. 276.7° C. (int. 13).

(d) A mixture of 10.6 parts of N-[4-[4-(4-methoxyphenyl)-1-piperazinyl]phenyl]-5-methyl-1,3,4-thiadiazol-2-amine, 0.5 parts of bromoethane, 4 parts of sodium hydroxide pellets and 188 parts of N,N-dimethylformamide was stirred for 4 hours at 40°-50° C. After the addition of water, the crystallized product was filtered off and purified by column chromatography over silica gel using a mixture of trichloromethane, methanol, ethyl acetate and hexane (48:2:30:20 by volume) as eluent. The first fraction was collected and the eluent was evaporated. The residue was crystallized from 4-methyl-2-pentanone. The product was filtered off and dried, yielding 2.9 parts (25.3%) of N-(3-ethyl-5-methyl-1,3,4-thiadiazol-2(3H)-ylidene)-4-[4-(4-methoxyphenyl)-1-piperazinyl]benzenamine; mp. 175.4° C. (int. 14). The second fraction was collected and the eluent was evaporated. The residue was crystallized from 4-methyl-2-pentanone. The product was filtered off and dried, yielding 6.5 parts (56.7%) of N-ethyl-N-[4-[4-(4-methoxyphenyl)-1-piperazinyl]phenyl]-5-methyl-1,3,4-thiadiazol-2-amine; mp. 186.8° C. (int. 15).

Example 5

To a stirred mixture of 17.2 parts of phenyl [4-[4-(4-methoxy-3,5-dimethylphenyl)-1-piperazinyl]phenyl]-carbamate, 225 parts of N,N-dimethylformamide and 9.1 parts of N,N-diethylethanamine were added 9.6 parts of chlorotrimethylsilane. The whole was stirred first for 2 hours at room temperature and further for 2 hours at 80° C. After cooling, 10.1 parts of 2-bromoethanamine hydrobromide were added and stirring was continued for 1 hour. The resulting solution was added to a stirred mixture of 9.2 parts of a sodium hydride dispersion 50% and 45 parts of N,N-dimethylformamide. After stirring for 2 hours at room temperature, 6.15 parts of 1-bromopropane were added dropwise. Upon completion, stirring was continued overnight at room temperature. The reaction mixture was poured into water. The precipitated product was filtered off and crystallized from 2-propanol, yielding 5.6 parts (33.1%) of 1-[4-[4-(4-methoxy-3,5-dimethylphenyl)-1-piperazinyl]phenyl]-3-propyl-2-imidazolidinone (int. 16).

Example 6

A mixture of 50 parts of phenyl [4-[4-(4-methoxyphenyl)-1-piperazinyl]phenyl]carbamate, 22.7 parts of ethyl 2-piperidinecarboxylate, 4 parts of N,N-dimethyl-4-pyridinamine and 300 parts of 1,4-dioxane was stirred for 5 hours at reflux temperature. After saturation with water, the reaction mixture was heated for 30 minutes. After cooling, the precipitated product was filtered off, washed with 2-propanol and purified by column chromatography over silica gel using a mixture of trichloromethane and methanol (99:1 by volume) as eluent. The pure fractions were collected and the eluent was evaporated. The residue was crystallized from 1-butanol. The product was filtered off and dried, yielding 24.8 parts (47.5%) of 5,6,7,8-tetrahydro-2-[4-[4-(4-methoxyphenyl)-1-piperazinyl]phenyl]imidazo[1,5-a]pyridine-1,3(2H,8aH)-dione; mp. 223.4° C. (int. 17).

Example 7

(a) To a stirred and cooled (ice-bath) mixture of 15 parts of 1-(4-nitrophenyl)hydrazine and 160 parts of absolute ethanol were added 13.5 parts of ethyl ethanimidate hydrochloride. After stirring for 3 hours while cooling, the reaction mixture was poured into water. The precipitated product was filtered off, washed with water and dried, yielding 19 parts (85%) of 1-(1-ethoxyethylidene)-2-(4-nitrophenyl)hydrazine; mp. 101.8° C. (int. 18).

(b) A mixture of 10 parts of 1-(1-ethoxyethylidene)-2-(4-nitrophenyl)hydrazine, 13 parts of morpholine and 135 parts of methylbenzene was stirred and refluxed for 72 hours. The reaction mixture was cooled. The precipitated product was filtered off, washed with methylbenzene and dried, yielding 8 parts (67%) of 1-[1-(4-morpholinyl)ethylidene]-2-(4-nitrophenyl)hydrazine; mp. 175.9° C. (int. 19)

(c) A mixture of 13 parts of 1-[1-(4-morpholinyl)ethylidene-2-(4-nitrophenyl)hydrazine, 8.5 parts of 1-isocyanatopropane, 1 part of N,N-dimethyl-4-pyridinamine and 39 parts of dichloromethane was stirred and refluxed for 2 hours. The whole was evaporated and 90 parts of dimethylbenzene were added to the residue. Stirring at reflux was continued for 3 hours. The reaction mixture was cooled and filtered over diatomaceous earth. The filtrate was saturated with petroleum ether. The precipitated product was filtered off and crystallized from 2-propanol, yielding 8.5 parts (65%) of 2,4-dihydro-5-methyl-2-(4-nitrophenyl)-4-propyl-3H-1,2,4-triazol-3-one; mp. 125.4° C. (int. 20).

(d) A mixture of 57 parts of 2,4-dihydro-5-methyl-2-(4-nitrophenyl)-4-propyl-3H-1,2,4-triazol-3-one and 400 parts of methanol was hydrogenated at normal pressure and at room temperature with 5 parts of palladium-on-charcoal catalyst 20%. After the calculated amount of hydrogen was taken up, the catalyst was filtered off and the filtrate was evaporated. The residue was crystallized from a mixture of 4-methyl-2-pentanone and 2,2'-oxybispropane. The product was filtered off and dried, yielding 46 parts (91%) of 2-(4-aminophenyl)-2,4-dihydro-5-methyl-4-propyl-3H-1,2,4-triazol-3-one, mp. 138.8° C. (int. 21).

(e) A mixture of 25 parts of N,N-bis(2-chloroethyl)-4-methoxybenzenamine, 23.2 parts of 2-(4-aminophenyl)-2,4-dihydro-5-methyl-4-propyl-3H-1,2,4-triazol-3-one, 2 parts of potassium iodide and 200 parts of cyclohexanol was stirred and refluxed for 5 hours using a water-separator. The reaction mixture was cooled and neutralized with a sodium hydrogen carbonate solution. The product was filtered off and dissolved in trichloromethane. The solution was filtered over silica gel and the solvent was evaporated. The residue was crystallized from 1-butanol, yielding 18 parts (44%) of 2,4-dihydro-2-[4-[4-(4-methoxyphenyl)-1-piperazinyl]phenyl]-5-methyl-4-propyl-3H-1,2,4-triazol-3-one; mp. 202.2° C. (int. 22).

Example 8

(a) To a stirred solution of 42.8 parts of sodium hydride dispersion 50% in 200 parts of dimethyl sulfoxide was added dropwise slowly a solution of 50 parts of 2,4(1H,3H)-pyrimidinedione in 800 parts of dimethyl sulfoxide while the temperature was kept constant (20° C.) by cooling in an ice/water bath. 62.9 Parts of 1-fluoro-4-nitrobenzene were added and the whole was stirred overnight at 50° C. After cooling, the reaction mixture was poured into 2500 parts of water. The whole was washed with dichloromethane. The aqueous phase was brought to pH 5-6. The product was filtered off and stirred in 2-propanone. The product was filtered off and dried in vacuo at 60° C., yielding 60 parts (57.6%) of 1-(4-nitrophenyl)-2,4(1H,3H)-pyrimidinedione; mp.>300° C. (int. 23).

(b) A mixture of 3 parts of 1-(4-nitrophenyl)-2,4(1H,3H)-pyrimidinedione, 1,4 parts of potassium hydroxide and 67.5 parts of N,N-dimethylacetamide was stirred for 1 hour at room temperature under nitrogen atmosphere. 1.52 Parts of bromoethane were added and stirring was continued overnight at room temperature. The reaction mixture was poured into 100 parts of ice water. The product was filtered off and stirred in methanol. The product was filtered off and dried in vacuo at 60° C., yielding 2.4 parts (65.6%) of 3-ethyl-1-(4-nitro-phenyl)-2,4(1H,3H)-pyrimidinedione; mp. 182.5° C. (int. 24).

(c) A mixture of 28.4 parts of 3-ethyl-1-(4-nitrophenyl)-2,4(1H,3H)-pyrimidinedione, 5 parts of a solution of thiophene in methanol 4% and 500 parts of 2-methoxyethanol was hydrogenated at normal pressure and at 50° C. with 3 parts of platinum-on-charcoal catalyst 5%. After the calculated amount of hydrogen was taken up, the catalyst was filtered off and the filtrate was concentrated to a volume of about 150 parts. After cooling, the product was filtered off (the filtrate was set aside) and dried in vacuo at 60° C., yielding a first fraction of 16.5 parts of 1-(4-aminophenyl)-3-ethyl-2,4(1H,3H)-pyrimidinedione (int. 25). The filtrate, which was set aside (see above), was evaporated. The residue was stirred in methanol. The product was filtered off and dried in vacuo at 60° C., yielding a second fraction of 5.7 parts of int. 20. Total yield: 22.2 parts (88.3%) of int. 25; mp. 190.8° C.

(d) A mixture of 17.47 parts of N,N-bis(2-chloroethyl)-4-methoxybenzenamine, 16.3 parts of 1-(4-aminophenyl)-3-ethyl-2,4(1H,3H)-pyrimidinedione, 11.83 parts of sodium hydrogen carbonate and 240 parts of 1-butanol was stirred for 24 hours at reflux temperature. After cooling, 150 parts of water were added. The product was filtered off and crystallized from methylbenzene. The product was filtered off and dried in vacuo at 60° C., yielding 10.6 parts (37.0%) of 3-ethyl-1-[4-[4-(4-methoxyphenyl)-1-piperazinyl]phenyl]-2,4(1H,3H)-pyrimidinedione; mp. 210.2° C. (int. 26).

Example 9

(a) A mixture of 40 parts of 2-(4-nitrophenyl)-1,2,4-triazine-3,5-(2H,4H)-dione, 25.7 parts of 1-bromobutane, 26.25 parts of potassium carbonate and 720 parts of N,N-dimethylformamide was stirred overnight at 45° C. The reaction mixture was poured into 2000 parts of ice water. The precipitated product was filtered off, washed with water and 2,2'-oxybispropane and stirred in methanol. The product was filtered off and dried in vacuo at 70° C., yielding 33.9 parts (68.6%) of 4-butyl-2-(4-nitrophenyl)-1,2,4-triazine-3,5(2H,4H)-dione (int. 27).

(b) A mixture of 33.9 parts of 4-butyl-2-(4-nitrophenyl)-1,2,4-triazine-3,5(2H,4H)-dione, 2 parts of a solution of thiophene in methanol 4% and 400 parts of 2-methoxyethanol was hydrogenated at normal pressure and at room temperature with 3 parts of palladium-on-charcoal catalyst 10%. After the calculated amount of hydrogen was taken up, the catalyst was filtered off and the filtrate was evaporated, yielding 29 parts (92.8%) of 2-(4-aminophenyl)-4-butyl-1,2,4-triazine-3,5(2H,4H)-dione as a residue (int. 28).

(c) A mixture of 27.1 parts of N,N-bis(2-chloroethyl)-4-methoxybenzenamine, 29 parts of 2-(4-aminophenyl)-4-butyl-1,2,4-triazine-3,5(2H,4H)-dione, 18.4 parts of sodium hydrogen carbonate and 350 parts of 2-methyl-2-propanol was stirred overnight at reflux temperature. After cooling, 200 parts of water was added. The precipitated product was filtered off and crystallized from 4-methyl-2-pentanone. The product was filtered off and dried in vacuo at 75° C., yielding 19.8 parts (41.3%) of 4-butyl-2-[4-[4-(4-methoxyphenyl)-1-piperazinyl]phenyl]-1,2,4-triazine-3,5(2H,4H)-dione; mp. 181.3° C. (int. 29).

Example 10

(a) To 900 parts of tetrahydrofuran, cooled in an ice-bath, were added portionwise 156 parts of aluminum chloride and the whole was stirred vigorously till all solid entered solution. This solution was added quickly to a stirred suspension of 208 parts of sodium azide in 225 parts of tetrahydrofuran and stirring was continued for 1 hour at reflux temperature. After cooling to room temperature, there was added dropwise a solution of 54 parts of butanoyl chloride, 225 parts of tetrahydrofuran at a temperature below 30° C. The whole was heated slowly to reflux and stirring was continued overnight at reflux temperature. While cooling, the reaction mixture was acidified with 800 parts of hydrochloric acid solution 6N and the whole was evaporated. The residue was stirred in a sodium hydrogen carbonate solution and washed with trichloromethane. The aqueous layer was acidified with concentrated hydrochloric acid and the whole was evaporated. The residue was stirred in 2-propanone. The precipitate was filtered off and the filtrate was evaporated, yielding 32 parts of 1,4-dihydro-1-propyl-5H-tetrazol-5-one as a residue (int. 30).

(b) A mixture of 38 parts of 1-fluoro-4-nitrobenzene, 32 parts of 1,4-dihydro-1-propyl-5H-tetrazol-5-one, 14 parts of sodium carbonate and 200 parts of dimethyl sulfoxide was stirred and heated for 4 hours at 120° C. The reaction mixture was cooled and poured into water. The precipitated product was filtered off and crystallized from 2-propanol, yielding 46 parts (74%) of 1,4-dihydro-1-(4-nitrophenyl)-4-propyl-5H-tetrazol-5-one; mp. 91.1° C. (int. 31).

(c) A mixture of 43 parts of 1,4-dihydro-1-(4-nitropheyl)-4-propyl-5H-tetrazol-5-one and 400 parts of methanol was hydrogenated at normal pressure and at room temperature with 4 parts of palladium-on-charcoal catalyst 10%. After the calculated amount of hydrogen was taken up, the catalyst was filtered off and the filtrate was evaporated. The residue was converted into the hydrochloride salt in 2-propanol. The salt was filtered off and dried, yielding 39 parts (90%) of 1-(4-aminophenol)-1,4-dihydro-4-propyl-5H-tetrazol-5-one monohydrochloride; mp. 203° C. (int. 32).

(d) A mixture of 25 parts of N,N-bis(2-chloroethyl)-4-methoxybenzenamine, 25.5 parts of 1-(4-aminophenyl)-1,4-dihydro-4-propyl-5H-tetrazol-5-one monohydrochloride, 2 parts of potassium iodide and 200 parts of cyclohexanol was stirred and refluxed for 5 hours using a water-separator. The reaction mixture was cooled and neutralized with a sodium hydrogen carbonate solution. The product was filtered off and crystallized from 1-butanol, yielding 15.5 parts (39%) of 1,4-dihydro-1-[4-[4-(4-methoxyphenyl)-1-piperazinyl]-phenyl]-4-propyl-5H-tetrazol-5-one; mp. 189.7 ° C. (int. 33).

Example 11

(a) To a stirred mixture of 54.3 parts of 3-bromo-4-[4-(4-methoxyphenyl)-1-piperazinyl]-benzenamine and 189 parts of tetrahydrothiophene 1,1-dioxide was added portionwise, during a 30 minutes-period, 28.6 parts of ethyl[(dimethylamino)methylene]hydrazinecarboxylate at 160° C. Upon completion, stirring and heating were continued at 170° C. till all ethanol was distilled off. After cooling to room temperature, 120 parts of 4-methyl-2-pentanone were added to dissolve the sticky residue. The whole was heated till a solution was obtained.

After cooling, the supernatant phase was decanted and the residue was stirred in 2,2'-oxybispropane. The product was filtered off and dried, yielding 44.6 parts of 4-[3-bromo-4-[4-(4-methoxyphenyl)-1-piperazinyl]-phenyl]-2,4-dihydro-3H-1,2,4-triazol-3-one (int. 34).

(b) To a stirred mixture of 45 parts of 4-[3-bromo-4-[4-(4-methoxyphenyl)-1-piperazinyl]-phenyl]-2,4-dihydro-3H-1,2,4-triazol-3-one and 90 parts of dimethyl sulfoxide were added 15 parts of potassium hydroxide (pulverized). Then there were added 6.2 parts of 2-bromobutane and the whole was stirred for 20 hours at room temperature. The reaction mixture was poured into water. The produce was extracted with trichloromethane. The extract was dried, filtered and evaporated. The residue was purified by column chromatography over silica gel using a mixture of trichloromethane and methanol (99:1 by volume) as eluent. The pure fractions were collected and the eluent was evaporated. The residue was crystallized from a mixture of methylbenzene and hexane (1:2 by volume). The precipitated product was filtered off and recrystallized from 80 parts of methanol. The product was filtered off and dried in vacuo at 60° C., yielding a first fraction of 14.7 parts (29.8%) of 4-[3-bromo-4-[4-(4-methoxyphenyl)-1-piperazinyl]phenyl]-2,4-dihydro-2-(1-methylpropyl)-3H-1,2,4-triazol-3-one; mp. 144.6° C. The less pure fractions were collected and the eluent was evaporated. The residue was further purified by column chromatography (HPLC) over silica gel using a mixture of ethyl acetate and methanol (97:3 by volume) as eluent. The pure fractions were collected and the eluent was evaporated. The residue was crystallized from methanol, yielding a second fraction of 4-[3-bromo-4-[4-(4-methoxyphenyl)-1-piperazinyl]-phenyl]-2,4-dihydro-2-(1-methylpropyl)-3H-1,2,4-triazol-3-one; mp. 144.7° C. (int. 35).

Example 12

(a) To a stirred solution of 25.0 parts of 2,2,2-trifluoroethanol in 175 parts of N,N-diethylethanamine were added portionwise 62.2 parts of 2-naphthalenesulfonyl chloride. Upon completion, a mixture of 1.5 parts of N,N-dimethyl-4-pyridinamine and 25 parts of ethyl acetate was added during a period of 20 minutes. Upon complete addition, stirring was continued overnight at room temperature. The reaction mixture was filtered and the filtrate was evaporated in vacuo. The residue was stirred in water and solidified product was filtered off under reduced pressure. The precipitated product was dissolved in dichloromethane. The organic layer was dried, filtered and evaporated in vacuo. The residue was treated with petroleum ether. After filtration, the precipitated product was crystallized from 2-propanol. The product was filtered off and dried, yielding 65.3 parts (89%) of 2,2,2-trifluoroethyl 2-naphthalenesulfonate; mp. 72.7° C. (int. 36).

(b) A mixture of 17.5 parts of 2,4-dihydro-4-[4-[4-(4-methoxyphenyl)-1-piperazinyl]-phenyl]-3H-1,2,4-triazol-3-one prepared as described in example XVII of U.S. Pat. No. 4,267,179, 19.5 parts of 2,2,2-trifluoroethyl 2-naphthalenesulfonate, 10.0 parts of potassium carbonate and 135 parts of N,N-dimethylformamide was stirred overnight at 145° C. After cooling, water was added. The crystallized product was filtered off under pressure and dissolved in dichloromethane. The organic layer was dried, filtered and evaporated in vacuo. The residue was purified by column chromatography over silica gel using trichloromethane as eluent. The pure fractions were collected and the eluent was evaporated. The residue was crystallized from 2-butanone. The product was filtered off and dried, yielding 9.2 parts (42.4%) of 2,4-dihydro-4-[4-[4-(4-methoxyphenyl)-1-piperazinyl]phenyl]-2-(2,2,2-trifluoroethyl)-3H-1,2,4-triazol-3-one; mp. 208.0° C. (int. 37).

B. Preparation of Final Compounds

Example 13

A mixture of 16 parts of 4,5-dihydro-2-[4-[4-(4-methoxyphenyl)-1-piperazinyl]phenyl]-5-methyl-4-propyl-3H-1,2,4-triazol-3-one and 375 parts of a hydrobromic acid solution 48% in water was stirred and refluxed for 4 hours. After cooling, the precipitated product was filtered off and dissolved in a mixture of methanol and water. The whole was neutralised with a sodium hydrogen carbonate solution. The precipitated product was filtered off and crystallized from 1,4-dioxane, yielding 13 parts (85%) of 4,5-dihydro-2-[4-[4-(4-hydroxyphenyl)-1-piperazinyl]phenyl]-5-methyl-4-propyl-3H-1,2,4-triazol-3-one; mp. 252.9° C. (compound 8.10).

Example 14

A mixture of 31 parts of 5,6,7,8-tetrahydro-2-[4-[4-(4-methoxyphenyl)-1-piperazinyl]-phenyl]imidazo[1,5-a]pyridine-1,3(2H,8aH)-dione, 300 parts of a hydrobromic acid solution 48% in water and 100 parts of acetic acid, saturated with hydrogen bromide was stirred for 4 hours at reflux temperature. On the addition of 300 parts of water, the product was allowed to crystallize. After cooling, the product was filtered off, washed with water, dissolved in a mixture of methanol and water and then the solution was neutralized with a sodium hydrogen carbonate solution. The product was filtered off, washed with water and 2-propanol and dried, yielding 24.5 parts (81%) of 5,6,7,8-tetrahydro-2-[4-[4-(4-hydroxyphenyl)-1-piperazinyl]phenyl]imidazo[1,5a]pyridine-1,3(2H,8aH)-dione (compound 5.09).

Example 15

A mixture of 6.3 parts of N-ethyl-4,5-dihydro-5-methoxy -N-[4-[4-(4-methoxyphenyl)-1-piperazinyl]-phenyl]-2-thiazolamine hemihydrate, 1 part of sodium sulfite and 150 parts of a hydrobromic acid solution 48% in water was stirred for 12 hours at reflux temperature. The reaction mixture was evaporated in vacuo and the residue was dissolved in a mixture of trichloromethane and water. The solution was neutralized with a sodium hydrogen carbonate solution and the produce was extracted with 1500 parts of trichloromethane. The extract was dried, filtered and evaporated in vacuo. The residue was crystallized from 2-propanol. The product was filtered off and dried, yielding 4.5 parts (81.5%) of 4-[4-[4-[ethyl(2-thiazolyl)-amino]phenyl]-1-piperazinyl]phenol; mp. 214.6° C. (compound 3.08).

Example 16

To a stirred mixture of 300 parts of a hydrobromic acid solution 48% in water, 100 parts of a hydrobromic acid solution in acetic acid and 2 parts of sodium hydrogen sulfite were added 18.9 parts of 4-butyl-2-[4-[4-(4-methoxyphenyl)-1-piperazinyl]phenyl]-1,2,4-triazine-3,5(2H,4H)-dione. Stirring was continued for 5 hours at reflux temperature. After cooling, the precipitated product was filtered off and dissolved in a mixture of water and methanol. The mixture was neutralized with a saturated sodium hydrogen carbonate solution. The precipitated product was filtered off and crystallized twice; first from 4-methyl-2-pentanone and then from 1-propanol. The product was filtered off and dried in vacuo at 75° C., yielding 9.1 parts (50.2%) of 4-butyl-2-[4-[4-(4-hydroxyphenyl)-1-piperazinyl]phenyl]-1,2,4-triazine-3,5(2H,4H)-dione; mp. 202.3° C. (compound 10.05).

Example 17

A mixture of 4.5 parts of 4-(1-piperazinyl)phenol, 5.5 parts of 1-chloro-2,4-dinitrobenzene, 2.6 parts of sodium carbonate and 90 parts of N,N-dimethylacetamide was stirred overnight at 50° C. After cooling, the mixture was poured into ice water and the product was extracted twice with 4-methyl-2-pentanone. The undissolved product was dissolved in 2-propanol. This solution and the combined organic layers were washed with water, dried, filtered and evaporated. The residue was converted into the hydrochloride salt in 2-propanol. The salt was filtered off and crystallized twice: first from a mixture of 2-propanol and water (10:1 by volume) and then from a mixture of methanol and water (10:1 by volume). The product was filtered off and dried, yielding 3.9 parts (37.7%) of 4-[4-(2,4-dinitrophenyl)-1-piperazinyl]-phenol monohydrochloride, methanol(1:1); mp. 178.0° C. (compound 1.13).

Example 18

A mixture of 123.8 parts of 2-methyl-4-(1-piperazinyl)phenol dihydrobromide, 49.4 parts of 1-fluoro-4-nitrobenzene, 58.2 parts of sodium carbonate and 300 parts of dimethyl sulfoxide was stirred over weedend at room temperature. The reaction mixture was poured into water. The product was filtered of, washed with 2-propanol and dried, yielding 101.2 parts (92.3%) of 2-methyl-4-[4-(4-nitrophenyl)-1-piperazinyl]phenol as a solid residue (compound 1.12).

Example 19

A mixture of 5.4 parts of 4-(1-piperazinyl)phenol, 4.77 parts of 1,4-difluoro-2-nitrobenzene and 160 parts of 1-butanol was stirred and refluxed overnight. The reaction mixture was cooled and poured into alkaline water. The product was extracted with dichloromethane. The extract was dried, filtered and evaporated. The residue was purified by column chromatography over silica gel using a mixture of trichloromethane and methanol (98:2 by volume) as eluent. The pure fractions were collected and the eluent was evaporated. The residue was converted into the hydrochloride salt in 2-propanol. The salt was filtered off and dried, yielding 8.3 parts (78.2%) of 4-[4-(4-fluoro-2-nitrophenyl)-1-piperazinyl]phenol monohydrochloride; mp. 197.0°–210° C. (dec.) (compound 1.16).

Example 20

To a stirred solution of 10.8 parts of 4-[4-(4-aminophenyl)-1-piperazinyl]phenol in 3.2 parts of pyridine and 90 parts of N,N-dimethylformamide was added dropwise a solution of 3.1 parts of acetyl chloride in 27 parts of methylbenzene at 20° C. (exothermic reaction). Upon completion, stirring was continued for 1 hour at 20° C. The reaction mixture was poured into water while stirring. The product was filtered off, washed with water and dissolved in a mixture of trichloromethane and methanol (3:1 by volume). The whole was purified by column chromatography over silica gel using a mixture of trichloromethane and methanol (95:5 by volume) as eluent. The second fraction was collected and the eluent was evaporated. The residue was crystallized from a mixture of ethanol and methylbenzene (1:1 by volume)+(activated charcoal). The produce was filtered off and dried yielding 5.3 parts (42.5%) of N-[4-[4-(4-hydroxyphenyl)-1-piperazinyl]phenyl]acetamide; mp. 256.2° C. (compound 1.03).

Example 21

A mixture of 6 parts of 2-[1-(4-chlorobenzoyl)-propyl]-2,4-dihydro-4-[4-[4-[(4-hydroxyphenyl)-1-piperazinyl]phenyl]-3H-1,2,4-triazol-3-one, 103 parts of 1,4-dioxane and 40 parts of methanol was stirred at room temperature, while a solution of 1.5 parts of sodium tetrahydroborate in 25 parts of water was slowly added dropwise. Upon completion, stirring was continued for 1 hour at room temperature. The reaction mixture was poured into 1500 parts of water, to which a few parts of acetic acid were added. After stirring for 30 minutes, the precipitated product was filtered off, washed with water and methanol and dried, yielding 5.7 parts (95.3%) of 2-[1-[(4-chlorophenyl)-hydroxymethyl]propyl]-2,4-dihydro-4-[4[4(4-hydroxyphenyl)-1-piperazinyl]phenyl]-3H-1,2,4-triazol-3-one; mp. 269.9° C. (compound 7.43).

All compounds listed in Table 1 to 11 were obtained following the procedure of the example referred to in the column Ex. No..

TABLE 1

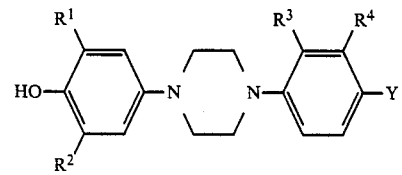

| Comp. | R¹ | R² | R³ | R⁴ | Y | Physical data | Ex. No. |
|---|---|---|---|---|---|---|---|
| 1.01 | H | H | H | H | —NO$_2$ | mp. 260° C. | 17 |
| 1.02 | H | H | H | H | —NH$_2$ | crystals | 13 |
| 1.03 | H | H | H | H | —NHCOCH$_3$ | mp. 256.2° C. | 20 |
| 1.04 | H | H | H | H | —NHCH(CH$_3$)C$_2$H$_5$ | 2HBr/mp. 196.5° C. | 13 |
| 1.05 | H | H | H | H | —CH$_3$ | mp. 181.7° C. | 14 |
| 1.06 | H | H | H | H | —COCH$_3$ | HCl/mp. 225.3° C. | 17 |
| 1.07 | H | H | H | H | —OH | mp. 290.5° C. | 14 |
| 1.08 | H | H | H | H | —Cl | HBr/mp. 246.5° C. | 14 |
| 1.09 | Cl | H | H | H | —NO$_2$ | residue | 13 |

TABLE 1-continued

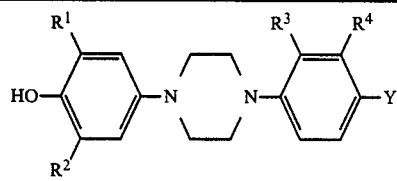

| Comp. | R¹ | R² | R³ | R⁴ | Y | Physical data | Ex. No. |
|---|---|---|---|---|---|---|---|
| 1.10 | CH₃ | CH₃ | H | H | —NO₂ | mp. 194.8° C. | 18 |
| 1.11 | CH₃ | CH₃ | H | H | —NO₂ | 2HBr/solid residue | 13 |
| 1.12 | CH₃ | H | H | H | —NO₂ | solid residue | 18 |
| 1.13 | H | H | NO₂ | H | —NO₂ | HCl/CH₃OH/mp. 178° C. | 17 |
| 1.14 | H | H | NO₂ | H | —H | HCl/mp. 216.1° C. | 17 |
| 1.15 | H | H | H | CF₃ | —H | HBr/mp. 199.3° C. | 14 |
| 1.16 | H | H | NO₂ | H | —F | HCl/ mp. 197.2–210° C.(dec.) | 19 |
| 1.17 | H | H | NO₂ | H | —SO₂N(CH₃)₂ | mp. 196.3–197.7° C. | 19 |
| 1.18 | Cl | H | H | H | —NH₂ | mp. 210.2° C. | 13 |

TABLE 2

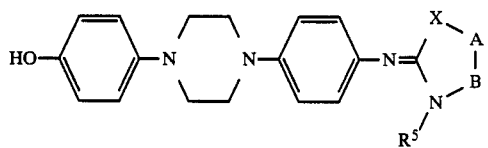

| Comp. | X | R⁵ | —A—B— | Physical data | Ex. No. |
|---|---|---|---|---|---|
| 2.01 | S | C₄H₉-n | —(CH₂)₃— | mp. 143.0° C. | 13 |
| 2.02 | S | CH₃ | —CH₂—C(CH₃)₂— | mp. 233.0° C. | 15 |
| 2.03 | S | CH₃ | —CH=CH— | mp. 225.0° C. | 15 |
| 2.04 | S | C₂H₅ | —CH=CH— | mp. 198.6° C. | 13 |
| 2.05 | S | C₃H₇-i | —CH=CH— | mp. 215.7° C. | 13 |
| 2.06 | S | CH(CH₃)C₂H₅ | —CH=CH— | mp. 160° C. | 15 |
| 2.07 | O | CH₃ | —(CH₂)₂— | mp. 217.1° C. | 13 |
| 2.08 | S | C₂H₅ | —C(CH₃)=N— | mp. 191.0° C. | 15 |
| 2.09 | S | C₂H₅ | —C(CH₃)₂—CH₂— | mp. 170.4° C. | 15 |
| 2.10 | S | C₂H₅ | —CH₂—CHCH₃— | mp. 171.3° C. | 15 |
| 2.11 | S | C₂H₅ | —(CH₂)₂— | mp. 208.3° C. | 15 |
| 2.12 | S | C₂H₅ | —CH₂—CH(C₆H₅)— | mp. 115° C. 0.5 H₂O | 15 |

TABLE 3

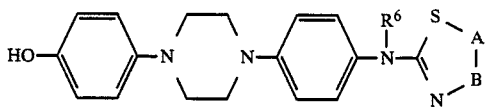

| Comp. | R⁶ | —A—B— | Physical data | Ex. No. |
|---|---|---|---|---|
| 3.01 | CH₃ | —CH₂—C(CH₃)₂— | mp. 197.7° C. | 15 |
| 3.02 | C₂H₅ | —CH₂—C(CH₃)₂— | mp. 200.9° C. | 15 |
| 3.03 | C₃H₇-n | —CH₂—C(CH₃)₂— | mp. 211.2° C. | 15 |
| 3.04 | C₃H₇-i | —CH₂—C(CH₃)₂— | mp. 210.0° C. | 15 |
| 3.05 | C₄H₉-n | —CH₂—C(CH₃)₂— | mp. 196.7° C. | 15 |
| 3.06 | CH(CH₃)C₂H₅ | —CH₂—C(CH₃)₂— | mp. 190.4° C. | 15 |
| 3.07 | CH₂—CH(CH₃)₂ | —CH₂—C(CH₃)₂— | mp. 203.7° C. | 15 |
| 3.08 | C₂H₅ | —CH=CH— | mp. 214.6° C. | 15 |
| 3.09 | C₂H₅ | —CH=C(CH₃)— | mp. 250.8° C. | 15 |
| 3.10 | C₂H₅ | —CH=C(C₆H₅)— | mp. 192.6° C. | 16 |
| 3.11 | C₂H₅ | —C(CH₃)=N— | mp. 218.3° C. | 15 |
| 3.12 | C₂H₅ | —C(CH₃)₂—CH₂— | mp. 225.2° C. | 15 |
| 3.13 | C₂H₅ | —CH₂—CH(CH₃)— | mp. 218.0° C. | 15 |
| 3.14 | C₂H₅ | —CH₂—CH(C₃H₇-i)— | mp. 165.9° C. | 15 |
| 3.15 | C₂H₅ | —CH₂—C(C₂H₅)₂— | mp. 157.1° C. | 15 |
| 3.16 | C₂H₅ | —CH₂—C(C₃H₇-n)₂— | mp. 112.2° C. | 15 |
| 3.17 | C₂H₅ | —CH₂—C(C₄H₉-n)₂— | mp. 116.9° C. | 15 |
| 3.18 | C₂H₅ | —(CH₂)₂—CH(CH₃)— | mp. 157.3° C. | 15 |
| 3.19 | C₂H₅ | —CH₂—C(C₂H₅)(CH₃)— | mp. 143.4° C. | 15 |
| 3.20 | C₂H₅ | —CH₂—C(C₅H₁₀-c)— | mp. 201.2° C. | 15 |

TABLE 3-continued

[Structure: HO-C6H4-N(piperazine)N-C6H4-N(R6)-C(=N-)-S-A-B]

| Comp. | R⁶ | —A—B— | Physical data | Ex. No. |
|---|---|---|---|---|
| 3.21 | C₂H₅ | —CH₂—(C₄H₈-c)— | mp. 205.1° C. | 15 |
| 3.22 | C₂H₅ | —(CH₂)₂— | mp. 232.0° C. | 15 |
| 3.23 | C₂H₅ | —CH₂—C(CH₃)(C₃H₇)— | mp. 144.7° C. | 15 |
| 3.24 | C₂H₅ | —CH₂—C(CH₃)(C₄H₉)— | mp. 153° C. | 15 |
| 3.25 | C₂H₅ | —CH₂—CH(C₆H₅) | mp. 219.2° C. | 15 |

TABLE 4

[Structure with R¹, R², hydroxyphenyl-piperazine-phenyl-N(R⁶)-C(=O)-CH₂-CR₂]

| Comp. | R¹ | R² | R⁶ | R | Physical data | Ex. No. |
|---|---|---|---|---|---|---|
| 4.01 | H | H | —CH₃ | H | solid residue | 13 |
| 4.02 | H | H | —C₂H₅ | H | mp. >300° C.(dec.) | 13 |
| 4.03 | H | H | —C₃H₇-n | H | solid residue | 13 |
| 4.04 | H | H | —C₃H₇-i | H | mp. 250° C. | 13 |
| 4.05 | H | H | —C₄H₉-n | H | mp. 217.5° C. | 13 |
| 4.06 | H | H | —CH(CH₃)C₂H₅ | H | mp. 220.4° C. | 16 |
| 4.07 | H | H | —(CH₂)₂OCH(CH₃)₂ | H | 0.5H₂O/mp. 178.3° C. | 13 |
| 4.08 | H | H | —CH(CH₃)COCH₃ | H | mp. 196.6° C. | 13 |
| 4.09 | H | H | —CH₃ | CH₃ | mp. 275.8° C. | 14 |
| 4.10 | H | H | —C₂H₅ | CH₃ | mp. 274.9° C. | 14 |
| 4.11 | H | H | —C₃H₇-n | CH₃ | mp. 252.1° C. | 14 |
| 4.12 | H | H | —C₃H₇-i | CH₃ | mp. 279.5° C. | 14 |
| 4.13 | H | H | —C₄H₉-n | CH₃ | mp. 238.5° C. | 14 |
| 4.14 | H | H | —CH(CH₃)C₂H₅ | CH₃ | mp. 266.2° C. | 14 |
| 4.15 | CH₃ | CH₃ | —C₃H₇-n | H | crystals | 13 |

TABLE 5

[Structure: HO-C6H4-N(piperazine)N-C6H4-N-C(=X)-N(R⁶)-C(R⁹)(R¹⁰)-C(=O)-]

| Comp. | X | R⁶ | R⁹ | R¹⁰ | Physical data | Ex. No. |
|---|---|---|---|---|---|---|
| 5.01 | O | C₃H₇-i | H | H | mp. 244.1° C. | 13 |
| 5.02 | O | C₄H₉-n | H | H | mp. 243.5° C. | 13 |
| 5.03 | O | C₄H₉-n | CH₃ | H | mp. 194.4° C. | 16 |
| 5.04 | O | CH₃ | CH₃ | CH₃ | mp. 291.0° C.(dec.) | 16 |
| 5.05 | O | C₂H₅ | CH₃ | CH₃ | mp. 246.9° C. | 13 |
| 5.06 | O | C₃H₇-i | CH₃ | CH₃ | mp. 269.9° C. | 16 |
| 5.07 | O | CH(CH₃)C₂H₅ | CH₃ | CH₃ | mp. 251.3° C. | 16 |
| 5.08 | O | CH(CH₃)COCH₃ | CH₃ | CH₃ | mp. 225.9° C. | 15 |
| 5.09 | O | —(CH₂)₄— | | H | solid residue | 14 |
| 5.10 | O | —(CH₂)₃— | | CH₃ | mp. 257.3° C. | 16 |
| 5.11 | O | CH₃ | —(CH₂)₅— | | mp. 260° C. | 14 |
| 5.12 | S | CH₃ | CH₃ | CH₃ | mp. 248.3° C. | 16 |
| 5.13 | S | C₂H₅ | CH₃ | CH₃ | mp. 230.2° C. | 14 |
| 5.14 | O | CH(CH₃)CO(4-Br—C₆H₅) | CH₃ | CH₃ | mp. 248.5° C. | 13 |

TABLE 6

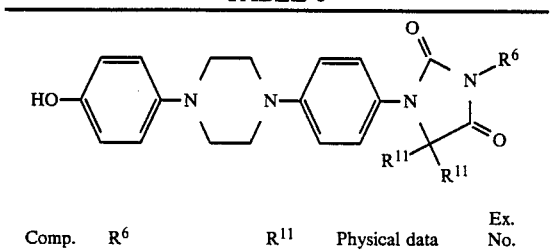

| Comp. | R⁶ | R¹¹ | Physical data | Ex. No. |
|---|---|---|---|---|
| 6.01 | $CH_3$ | H | solid residue | 13 |
| 6.02 | $C_2H_5$ | H | mp. 287.1° C. | 13 |
| 6.03 | $C_3H_7$-n | H | mp. 210.9° C. | 13 |
| 6.04 | $C_3H_7$-i | H | mp. 249° C. | 13 |
| 6.05 | $C_4H_9$-n | H | mp. 212.2° C. | 13 |
| 6.06 | $CH_3$ | $CH_3$ | mp. 268.2° C. | 13 |
| 6.07 | $C_2H_5$ | $CH_3$ | mp. 252.6° C. | 14 |
| 6.08 | $C_3H_7$-n | $CH_3$ | mp. 255.5° C. | 14 |
| 6.09 | $C_3H_7$-i | $CH_3$ | mp. 269° C. | 13 |
| 6.10 | $C_4H_9$-n | $CH_3$ | mp. 238.3° C. | 14 |
| 6.11 | $C_4H_9$-t | $CH_3$ | mp. 260° C. | 14 |
| 6.12 | $CH(CH_3)C_2H_5$ | $CH_3$ | mp. 244.7° C. | 14 |

TABLE 7

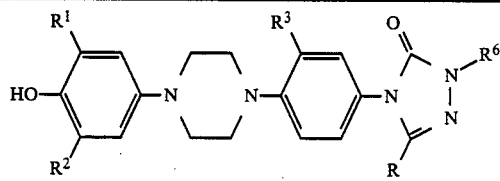

| Comp. | R¹ | R² | R³ | R⁶ | R | Physical data | Ex. No. |
|---|---|---|---|---|---|---|---|
| 7.01 | H | H | H | $CH_3$ | H | solid residue | 13 |
| 7.02 | H | H | H | $C_2H_5$ | H | mp. 217° C. | 13 |
| 7.03 | H | H | H | $C_3H_7$-n | H | solid residue | 13 |
| 7.04 | H | H | H | $C_3H_7$-i | H | mp. 208.4° C. | 13 |
| 7.05 | H | H | H | $C_4H_9$-n | H | mp. 221.6° C. | 13 |
| 7.06 | H | H | H | $CH(CH_3)C_2H_5$ | H | mp. 187.6° C. | 13 |
| 7.07 | H | H | H | $CH_2—CH(CH_3)_2$ | H | mp. 211.4° C. | 13 |
| 7.08 | H | H | H | $CH_2—CH_2—CH(CH_3)_2$ | H | mp. 216.6° C. | 14 |
| 7.09 | H | H | H | $C_5H_{11}$-n | H | mp. 202.1° C. | 16 |
| 7.10 | H | H | H | $C_5H_9$-c | H | mp. 229.1° C. | 14 |
| 7.11 | H | H | H | $CH_2—CF_3$ | H | mp. 219.0° C. | 15 |
| 7.12 | H | H | H | $CH(CH_3)CO—CH_3$ | H | mp. 192.2° C. | 15 |
| 7.13 | H | H | H | $CH(CH_3)CO—C_6H_5$ | H | mp. 249.3° C. | 16 |
| 7.14 | H | H | H | $CH(CH_3)CO$-(4-F—$C_6H_4$) | H | mp. 215.1° C. | 13 |
| 7.15 | H | H | H | $CH(CH_3)CO$-(4-Cl—$C_6H_4$) | H | mp. 225.7° C. | 16 |
| 7.16 | H | H | H | $CH(CH_3)CO$-(4-Br—$C_6H_4$) | H | mp. 211.1° C. | 15 |
| 7.17 | H | H | H | $CH(CH_3)CO$-(2,4-$Cl_2$—$C_6H_3$) | H | mp. 251.7° C. | 15 |
| 7.18 | H | H | H | ![2-methylcyclohexanone] | H | mp. 252.9° C. | 15 |
| 7.19 | H | H | H | $CH(CH_3)C_2H_5(S)$ | H | mp. 180.6° C. $[α]_D = +4.38°*$ | 15 |
| 7.20 | H | H | H | $CH(CH_3)CHOH—CH_3$ | H | mp. 209.7° C. | 21 |
| 7.21 | H | H | Br | $CH(CH_3)C_2H_5$ | H | mp. 236.3° C. | 13 |
| 7.22 | H | H | H | $CH(CH_3)CHOH(2,4-Cl_2—C_6H_3)$ | H | A/mp. 221.0° C. | 21 |
| 7.23 | H | H | H | $CH(CH_3)CHOH(2,4-Cl_2—C_6H_3)$ | H | B/mp. 255.2° C. | 21 |
| 7.24 | $CH_3$ | $CH_3$ | H | $C_2H_5$ | H | HBr/solid | 13 |
| 7.25 | $CH_3$ | $CH_3$ | H | $CH(CH_3)C_2H_5$ | H | crystals | 13 |
| 7.26 | Cl | H | H | $C_3H_7$-i | H | solid residue | 13 |
| 7.27 | Cl | H | H | $CH(CH_3)C_2H_5$ | H | solid residue | 13 |
| 7.28 | H | H | H | $CH_3$ | $CH_3$ | mp. 260° C. | 13 |
| 7.29 | H | H | H | $C_2H_5$ | $CH_3$ | mp. 287.8° C. | 13 |
| 7.30 | H | H | H | $C_3H_7$-n | $CH_3$ | mp. 258.2° C. | 13 |
| 7.31 | H | H | H | $C_3H_7$-i | $CH_3$ | mp. 251.3° C. | 13 |
| 7.32 | H | H | H | $C_4H_9$-n | $CH_3$ | mp. 262° C. | 13 |
| 7.33 | H | H | H | $CH(CH_3)C_2H_5$ | $CH_3$ | mp. 239.9° C. | 14 |
| 7.34 | H | H | H | $CH_2CH(CH_3)_2$ | $CH_3$ | mp. 268.7° C. | 13 |
| 7.35 | H | H | H | $CH(CH_3)CHOH$-(4-Br—$C_6H_4$) | H | mp. 257.8° C. | 21 |
| 7.36 | H | H | H | $CH(C_2H_5)CO$-(4-Br—$C_6H_4$) | H | mp. 222.7° C. | 16 |
| 7.37 | H | H | H | $CH(CH_3)CO$-(3-Cl—$C_6H_4$) | H | mp. 205.4° C. | 15 |
| 7.38 | $CH_3$ | H | H | $CH(CH_3)C_2H_5$ | $CH_3$ | mp. 232.1° C. | 15 |
| 7.39 | $CH_3$ | H | H | $CH(CH_3)CO$-(4-Br—$C_6H_4$) | $CH_3$ | mp. 252.8° C. | 15 |
| 7.40 | Cl | H | H | $CH(CH_3)C_2H_5$ | $CH_3$ | mp. 208.8° C. | 15 |
| 7.41 | H | H | H | $CH(C_2H_5)CO$-(4-Cl—$C_6H_4$) | H | mp. 223.8° C. | 14 |
| 7.42 | H | H | H | $CH(CH_3)CHOH$-(3-Cl—$C_6H_4$) | H | mp. 184.9° C. | 21 |
| 7.43 | H | H | H | $CH(C_2H_5)CHOH$-(4-Cl—$C_6H_4$) | H | mp. 269.9° C. | 21 |
| 7.44 | H | H | H | $CH(CH_3)CO$-(2,4-$Br_2$—$C_6H_3$) | H | mp. 242.0° C. | 16 |
| 7.45 | H | H | H | $CH(CH_3)CO$-(4-$CH_3$—$C_6H_4$) | H | mp. 218.7° C. | 14 |
| 7.46 | H | H | H | $CH(CH_3)CHOH$-(4-$CH_3$—$C_6H_4$) | H | mp. 259.8° C. | 21 |
| 7.47 | $CH_3$ | H | H | H | $CH_3$ | mp. 292.5° C. | 13 |
| 7.48 | Cl | H | H | H | $CH_3$ | mp. >300° C. | 15 |
| 7.49 | $CH_3$ | $CH_3$ | H | H | $CH_3$ | mp. 291.8° C. | 15 |
| 7.50 | $CH_3$ | $CH_3$ | H | $CH(CH_3)C_2H_5$ | $CH_3$ | mp. 190.5° C. | 13 |

TABLE 7-continued

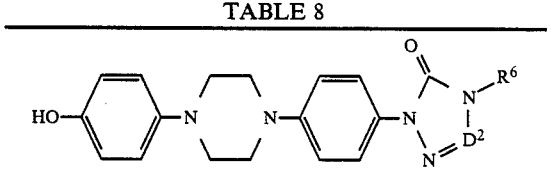

| Comp. | R¹ | R² | R³ | R⁶ | R | Physical data | Ex. No. |
|---|---|---|---|---|---|---|---|
| 7.51 | $CH_3$ | $CH_3$ | H | $CH(CH_3)CO$-$(4$-$Br$—$C_6H_4)$ | $CH_3$ | mp. 201.9° C. | 13 |
| 7.52 | Cl | H | H | $CH(CH_3)CO$-$(4$-$Br$—$C_6H_4)$ | $CH_3$ | mp. 219.9° C. | 15 |
| 7.53 | H | H | H | $CH(C_2H_5)CO$-$(2,4$-$Cl_2$—$C_6H_3)$ | H | mp. 215.0° C. | 14 |
| 7.54 | $CH_3$ | $CH_3$ | H | $CH(CH_3)CHOH$-$(4$-$Br$—$C_6H_4)$ | $CH_3$ | mp. 210.0° C. | 21 |
| 7.55 | H | H | H | $CH(CH_3)CH_2C_6H_5$ | H | mp. 222.7° C. | 16 |
| 7.56 | H | H | H | $CH(CH_3)CO$-$(2$-$Br,4$-$Cl$—$C_6H_3)$ | H | mp. 228.0° C. | 14 |
| 7.57 | H | H | H | $CH(CH_3)CO$-$(4$-$Br$—$C_6H_4)$ | $CH_3$ | mp. 236.4° C. | 14 |
| 7.58 | Cl | H | H | $CH(CH_3)CHOH$-$(4$-$Br$—$C_6H_4)$ | $CH_3$ | mp. 178.9° C. | 21 |
| 7.59 | H | H | H | $CH(CH_3)CO$-$(3$-$CF_3$—$C_6H_4)$ | H | mp. 192.2°C. | 14 |
| 7.60 | H | H | H | $CH(C_3H_7$-$n)CO$-$(2,4$-$Cl_2$—$C_6H_3)$ | H | mp. 164.2° C. | 14 |
| 7.61 | Cl | Cl | H | $CH(CH_3)C_2H_5$ | $CH_3$ | mp. 209.8° C. | 13 |
| 7.62 | H | H | H | $CH(C_2H_5)CO$-$(4$-$F$—$C_6H_4)$ | H | mp. 207.8° C. | 14 |
| 7.63 | H | H | H | $CH(C_2H_5)CHOH$-$(2,4$-$Cl_2$—$C_6H_3)$ | H | A/mp. 231° C. | 21 |
| 7.64 | H | H | H | $CH(C_2H_5)CHOH$-$(2,4$-$Cl_2$—$C_6H_3)$ | H | B/$H_2O$ mp. 218.1° C. | 21 |
| 7.65 | H | H | H | ![cycloheptanone structure] | H | mp. 250.4° C. | 16 |
| 7.66 | H | H | H | $CH(C_2H_5)COC_6H_5$ | H | mp. 200.7° C. | 14 |
| 7.67 | H | H | H | $CH(CH_3)CHOH(4$-$Br$—$C_6H_4)$ | H | A/mp. 207.1° C. | 21 |
| 7.68 | H | H | H | $CH(CH_3)CHOH(4$-$Br$—$C_6H_4)$ | H | B/mp. 264.7° C. | 21 |
| 7.69 | H | H | H | $CH(C_2H_5)CHOHC_6H_5$ | H | mp. 206.2° C. | 21 |
| 7.70 | H | H | H | $CH(CH_3)CHOH(4$-$Br$—$C_6H_4)$ | $CH_3$ | mp. 261.4° C. | 21 |
| 7.71 | H | H | H | $CH(C_3H_7$-$n)CHOH(2,4$-$Cl_2$—$C_6H_3)$ | H | A/mp. 231.6° C. | 21 |
| 7.72 | Cl | Cl | H | $CH(CH_3)CO(4$-$Br$—$C_6H_4)$ | $CH_3$ | | 13 |
| 7.73 | H | H | H | $CH(CH_3)CHOH$-$(3$-$CF_3$—$C_6H_4)$ | H | mp. 211.0° C. | 21 |
| 7.74 | H | H | H | $CH(C_3H_7$-$n)CHOH(2,4$-$Cl_2$—$C_6H_3)$ | H | B/0.5 $H_2O$ mp. 225.6° C. | 21 |
| 7.75 | H | H | H | $CH(CH_3)C_2H_5$ (R) | H | mp. 180.4° C. $[\alpha]_D = 4.16°*$ | 15 |
| 7.76 | H | H | H | $CH(CH_3)CO$-$(4$-$OCH_3$—$C_6H_4)$ | H | mp. 204.5° C. | 16 |
| 7.77 | H | H | H | $CH(CH_3)CO$-$(4$-$OH$-$C_6H_4)$ | H | mp. 199.8° C./ 0.5 $H_2O$ | 16 |
| 7.78 | H | H | H | $CH(CH_3)CO$-$(2,4$-$F_2$—$C_6H_3)$ | H | mp. 205.9° C. | 14 |
| 7.79 | H | H | H | $CH(CH_3)CO$-$(2$-$Cl$—$C_6H_4)$ | H | mp. 240° C. | 14 |

*c = 1% in methanol

TABLE 8

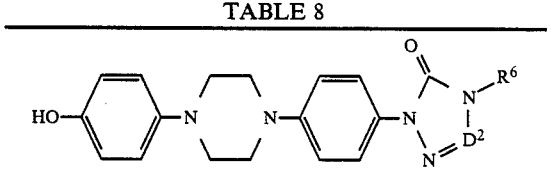

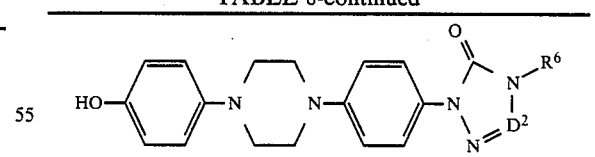

| Comp. | D² | R⁶ | Physical data | Ex. No. |
|---|---|---|---|---|
| 8.01 | =N— | $C_2H_5$ | mp. 226.2° C. | 13 |
| 8.02 | =N— | $C_3H_7$-$n$ | mp. 211° C. | 13 |
| 8.03 | =CH— | $CH_3$ | mp. 272.5° C. | 13 |
| 8.04 | =CH— | $C_2H_5$ | mp. 215.5° C. | 13 |
| 8.05 | =CH— | $C_3H_7$-$n$ | mp. 213.5° C. | 13 |
| 8.06 | =CH— | $C_3H_7$-$i$ | mp. 250.6° C. | 13 |
| 8.07 | =CH— | $CH(CH_3)C_2H_5$ | mp. 203.8° C. | 16 |
| 8.08 | =C(CH_3)— | $CH_3$ | mp. 265.7° C. | 13 |
| 8.09 | =C(CH_3)— | $C_2H_5$ | mp. 261.7° C. | 13 |
| 8.10 | =C(CH_3)— | $C_3H_7$-$n$ | mp. 252.9° C. | 13 |
| 8.11 | =C(CH_3)— | $C_3H_7$-$i$ | solid residue | 13 |

TABLE 9

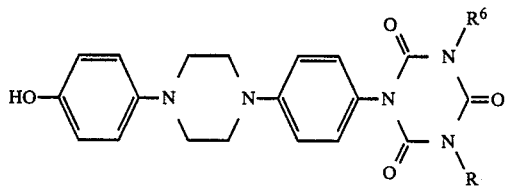

| Comp. | R[6] | R | Physical data | Ex. No. |
|---|---|---|---|---|
| 9.01 | $C_3H_7$-n | $CH_3$ | mp. 263.0° C. | 15 |
| 9.02 | $C_3H_7$-n | $C_2H_5$ | solid residue | 16 |
| 9.03 | $C_3H_7$-n | $C_3H_7$-n | $0.5H_2O$/mp. 225.7° C. | 16 |
| 9.04 | $C_2H_5$ | $C_3H_7$-i | mp. 263.1° C. | 16 |
| 9.05 | $CH_3$ | $CH_3$ | $0.5H_2O$/mp. 273.8° C. | 16 |
| 9.06 | $CH(CH_3)CO(4$-Br$—C_6H_4)$ | $C_3H_7$-i | mp. 235.7° C. | 16 |
| 9.07 | $CH(CH_3)CO(4$-Br$—C_6H_4)$ | $C_3H_7$-n | mp. 133.4° C. | 16 |
| 9.08 | $CH(CH_3)CHOH(4$-Br$—C_6H_4)$ | $C_3H_7$-i | mp. 234.2° C. | 21 |
| 9.09 | $CH(CH_3)CO(4$-Br$—C_6H_4)$ | $CH_3$ | mp. 256.5° C. | 16 |
| 9.10 | $CH(CH_3)CHOH(4$-Br$—C_6H_4)$ | $CH_3$ | mp. 223.4° C. | 21 |
| 9.11 | $CH(CH_3)CHOH(4$-Br$—C_6H_4)$ | $C_3H_7$-n | mp. 161.2° C. | 21 |

TABLE 10

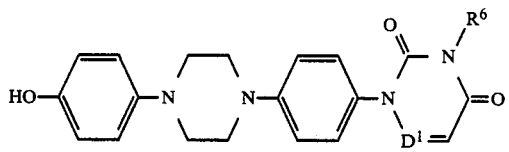

| Comp. | $D^1$ | R[6] | Physical data | Ex. No. |
|---|---|---|---|---|
| 10.01 | —N= | $CH_3$ | mp. 257.1° C. | 16 |
| 10.02 | —N= | $C_2H_5$ | mp. 215.6° C. | 15 |
| 10.03 | —N= | $C_3H_7$-n | mp. 189.3° C. | 15 |
| 10.04 | —N= | $C_3H_7$-i | mp. 207.3° C. | 16 |
| 10.05 | —N= | $C_4H_9$-n | mp. 202.3° C. | 16 |
| 10.06 | —N= | $CH(CH_3)C_2H_5$ | mp. 190.3° C. | 16 |
| 10.07 | —N= | $CH_2CH(CH_3)_2$ | mp. 208.8° C. | 16 |
| 10.08 | —CH= | $CH_3$ | solid residue | 13 |
| 10.09 | —CH= | $C_2H_5$ | mp. 258.4° C. | 13 |
| 10.10 | —CH= | $C_3H_7$-n | crystals | 13 |
| 10.11 | —CH= | $C_3H_7$-i | crystals | 13 |
| 10.12 | —CH= | $C_4H_9$-n | crystals | 13 |
| 10.13 | —CH= | $CH_2CH(CH_3)_2$ | crystals | 13 |

TABLE 11

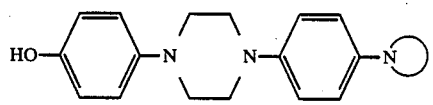

| Comp. | —N◯ | Physical data | Ex. No. |
|---|---|---|---|
| 11.01 | 1H-pyrazol-1-yl | solid residue | 13 |
| 11.02 | 1H-imidazol-1-yl | mp. 260° C. | 14 |
| 11.03 | 2-methyl-1H-imidazol-1-yl | mp. 300° C. | 13 |
| 11.04 | 2-(methylthio)-1H-imidazol-1-yl | mp. 288.4° C. | 13 |
| 11.05 | 3-(methylthio)-4H-1,2,4-triazol-4-yl | crystals | 14 |
| 11.06 | 3-methyl-5-(methylthio)-4H-1,2,4-triazol-4-yl | crystals | 14 |
| 11.07 | 3-hydroxy-4H-1,2,4-triazol-4-yl | mp. 300° C. | 13 |
| 11.08 | 1H-1,2,4-triazol-1-yl | mp. 276.6° C. | 14 |
| 11.09 | 3-(methylthio)-1H-1,2,4-triazol-1-yl | mp. 225.5° C. | 14 |
| 11.10 | 5-methyl-3-(methylthio)-1H-1,2,4-triazol-1-yl | mp. 255.8° C. | 14 |
| 11.11 | 5-methyl-1H-1,2,4-triazol-1-yl | mp. 281.1° C. | 13 |
| 11.12 | 5-ethyl-3-(methylthio)-1H-1,2,4-triazol-1-yl | mp. 232.6° C. | 13 |
| 11.13 | 5-propyl-1H-1,2,4-triazol-1-yl | mp. 225.6° C. | 13 |

C. Pharmacological Examples

The useful lipoxygenase inhibiting properties of the compounds of formula (I) are clearly demonstrated in the following test procedures.

Example 22

Arachidonate 5-lipoxygenase inhibition in Rat Basophilic Leukemia Cells Supernatant Rat basophilic leukemia (RBL) cells were grown as described (Adv. Prostaglandin Thromb. Leuk. Res., 11, 141-145). They were washed and suspended at $5 \times 10^7$ cells/ml in a 50 mM sodium phophate buffer (pH 7.4) containing 1 mM EDTA and 0.1% gelatin. The cells then were homogenized by sonification; the sonicate was centrifuged at $10,000 \times g$ for 60 min. The supernatant, aliquoted and stored at $-70°$ C., was used as the source of 5-lipoxygenase activity. The enzyme activity was assayed at 37° C. in a reaction mixture (total volume of 0.4 ml) containing 50 mM sodium phosphate buffer (pH 7.4), 2 mM ATP, 2 mM $CaCl_2$, 2 mM glutathion, the test compound ($10^{-5}$ to $10^{-8}$M) and the enzyme (60 mg protein). After a 5-min preincubation period, the reaction was started by the addition of 0.1 mCi of $^{14}$C-arachidonic acid and terminated 15 min later by the supplementation of 0.3 ml of an ice-cold mixture of ethyl ether:methanol:0.2 M citric cid (30:4:1). After shaking and centrifugation (3000×g, 5 min), the organic layer (N 150 ml) was removed, dried over anhydrous sodium sulfate and extracted with 1 ml ethyl acetate. The extract was then evaporated in vacuo and the residue dissolved in 20 ml of ethanol. Aliquots (20–30,000 cpm) were spotted on 0.25 mm silica coated plastic TLC sheets (Merck) and developed with chloroform:methanol:water:acetic acid (90:9:0.05:1). Radioactivity spots were located by autoradiography, cut out and their radioactivity determined by liquid scintillation counting. The counts present in the spots corresponding to arachidonic acid and the lipoxygenase product, 5-HPETE and LTB$_4$, were summed and the percentage of lipoxygenase products formation was calculated. For inhibition studies, concentration response curves and IC$_{50}$-values were obtained by determining the percentage of inhibition of lipoxygenase products formation in the presence of test compound compared with the uninhibited control. The first column of table 12 contains the percentage of inhibition of 5-lipoxygenase products formation (i.e. 5-HPETE and LTB$_4$) in the presence of 2.5 mM of a compound of formula (I).

Example 23

Inhibition of Dextran-induced edema formation in the ears of mice.

Intravenous injection of Dextran T500 ® (Pharmacia) and pontamine sky-blue dye into mice results in increased vascular permeability and edema formation, characterized by an intense blueing of the ears. Determination of the amount of extravasated dye is presumed to yield a quantitative measure of the 5-lipoxygenase inhibiting activity of the test compounds (Drug. Dev. Res. 8, 213–218, 1986). Unfasted male Swiss mice weighing 24–26 g were used in the experiments which were performed between 13.00 pm and 17.00 pm at an ambient temperature of 22±1° C. The mice were treated orally with a test compound of formula (I) dissolved in a volume of 150 ml of either polyethyleneglycol (PEG 200) or hydroxypropyl cyclodextrine at doses varying between 1.25 and 40 mg per kg bodyweight. In control experiments the mice were administered an identical amount of solvent alone. One hour after treatment there was injected intravenously an isotonic saline solution containing 60 mg/ml Dextran T500 ® and 13 mg/ml pontamine sky-blue dye in a volume of 0.1 ml per 10 g bodyweight. One hour and forty-five minutes later the animals were sacrificed by ether and their ears were removed. Extraction and quantification of the extravasated dye were performed as described (Drug Dev. Res. 8, 213–218, 1986). The calculated percentage of inhibition of ear blueing upon administration of a compound of formula (I) at a dose of 10 mg/kg bodyweight is shown in the second column of table 12.

TABLE 12

| Comp. no. | A | B |
| --- | --- | --- |
| 1.16 | 94 | — |
| 2.01 | 90 | 71 |
| 3.14 | — | 74 |
| 4.02 | 84 | — |
| 4.13 | 95 | — |
| 5.03 | 79 | 72 |
| 5.08 | 45 | 76 |

TABLE 12-continued

| Comp. no. | A | B |
| --- | --- | --- |
| 5.10 | 69 | 75 |
| 5.12 | 81 | 88 |
| 5.13 | 71 | 15 |
| 6.08 | 75 | 89 |
| 6.09 | 84 | — |
| 6.10 | 90 | 93 |
| 6.12 | 90 | 53 |
| 7.06 | 97 | — |
| 7.11 | 81 | 81 |
| 7.14 | 66 | 70 |
| 7.15 | 51 | 97 |
| 7.16 | 94 | 91 |
| 7.18 | 67 | 87 |
| 7.21 | 97 | — |
| 7.22 | 100 | 94 |
| 7.23 | 91 | 94 |
| 7.33 | 80 | 87 |
| 7.34 | 87 | 66 |
| 7.35 | 100 | 79 |
| 7.36 | 100 | 93 |
| 7.37 | 100 | 73 |
| 7.38 | 100 | 88 |
| 7.41 | — | 82 |
| 7.50 | 52 | 88 |
| 7.51 | 93 | 83 |
| 7.54 | 79 | 76 |
| 7.57 | 90 | 82 |
| 7.68 | — | 81 |
| 7.69 | — | 85 |
| 7.70 | — | 85 |
| 8.05 | 90 | — |
| 9.03 | 58 | 94 |
| 9.05 | — | 83 |
| 9.07 | — | 83 |
| 10.05 | 80 | — |

Column A: 5-lipoxygenase inhibition in RBL cells supernatant, % inhibition at 2.5 mM
Column B: inhibition of Dextran-induced blueing of the ears of mice, % inhibition at 10 mg/kg body weight
—: signifies not yet tested.

(D) Composition Examples

The following formulations exemplify typical pharmaceutical compositions in dosage unit form suitable for systemic administration to animal and human subjects in accordance with the present invention. "Active ingredient" (A.I.) as used throughout these examples relates to a compound of formula (I) or a pharmaceutically acceptable acid addition salt thereof.

Example 24

ORAL DROPS

500 Parts of the A.I. was dissolved in 0.5 l of 2-hydroxypropanoic acid and 1.5 l of the polyethylene glycol at 60°~80° C. After cooling to 30°~40° C. there were added 35 l of polyethylene glycol and the mixture was stirred well. Then there was added a solution of 1750 parts of sodium saccharin in 2.5 l of purified water and while stirring there were added 2.5 l of cocoa flavor and polyethylene glycol q.s. to a volume of 50 l, providing an oral drop solution comprising 10 mg/ml of A.I.. The resulting solution was filled into suitable containers.

Example 25

ORAL SOLUTION

9 Parts of methyl 4-hydroxybenzoate and 1 part of propyl 4-hydroxybenzoate were dissolved in 4 l of boiling purified water. In 3 l of this solution were dissolved first 10 parts of 2,3-dihydroxybutanedioic acid and thereafter 20 parts of the A.I. The latter solution was combined with the remaining part of the former solution and 12 l 1,2,3-propanetriol and 3 l of sorbitol 70% solution were added thereto. 40 Parts of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

Example 26

CAPSULES

20 Parts of the A.I., 6 parts sodium lauryl sulfate, 56 parts starch, 56 parts lactose, 0.8 parts colloidal silicon dioxide, and 1.2 parts magnesium stearate were vigorously stirred together. The resulting mixture was subsequently filled into 1000 suitable hardened gelatin capsules, comprising each 20 mg of the active ingredient.

Example 27

FILM-COATED TABLETS

Preparation of tablet core

A mixture of 100 psrts of the A.I., 570 parts lactose and 200 parts starch was mixed well and thereafter humidified with a solution of 5 parts sodium dodecyl sulfate and 10 parts polyvinylpyrrolidone (Kollidon-K 90 ®) in about 200 ml of water. The wet powder mixture was sieved, dried and sieved again. Then there was added 100 parts microcrystalline cellulose (Avicel ®) and 15 parts hydrogenated vegetable oil (Sterotex ®). The whole was mixed well and compressed into tablets, giving 10.000 tablets, each containing 10 mg of the active ingredient.

Coating

To a solution of 10 parts methyl cellulose (Methocel 60 HG ®) in 75 ml of denaturated ethanol there was added a solution of 5 parts of ethyl cellulose (Ethocel 22 cps ®) in 150 ml of dichloromethane. Then there were added 75 ml of dichloromethane and 2.5 ml 1,2,3-propanetriol. 10 Parts of polyethylene glycol was molten and dissolved in 75 ml of dichloromethane. The latter solution was added to the former and then there were added 2.5 parts of magnesium octadecanoate, 5 parts of polyvinylpyrrolidone and 30 ml of concentrated colour suspension (Opaspray K-1-2109 ®) and the whole was homogenated. The tablet cores were coated with the thus obtained mixture in a coating apparatus.

Example 28

INJECTABLE SOLUTION 1.8 Parts methyl 4-hydroxybenzoate and 0.2 parts propyl 4-hydroxybenzoate were dissolved in about 0.5 l of boiling water for injection. After cooling to about 50° C. there were added while stirring 4 parts lactic acid, 0.05 parts propylene glycol and 4 parts of the A.I.. The solution was cooled to room temperature and supplemented with water for injection q.s. ad 1 l, giving a solution comprising 4 mg/ml of A.I.. The solution was sterilized by filtration (U.S.P. XVII p. 811) and filled in sterile containers.

Example 29

SUPPOSITORIES 3 parts A.I. was dissolved in a solution of 3 parts 2,3-dihydroxybutanedioic acid in 25 ml polyethylene glycol 400. 12 Parts surfactant (SPAN ®) and triglycerides (Witepsol 555 ®) q.s. ad 300 parts were molten together. The latter mixture was mixed well with the former solution. The thus obtained mixture was poured into moulds at a temperature of 37°–38° C. to form 100 suppositories each containing 30 mg/ml of the A.I..

We claim:

1. A method of treating warm-blooded animals suffering from leukotriene-mediated diseases and disorders by administering an effective 5-lipoxygenase inhibiting amount of a compound of formula

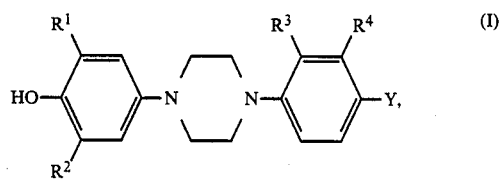

a pharmaceutically acceptable acid addition salt thereof or a stereochemically isomeric form thereof, wherein $R^1$ and $R^2$ each independently are hydrogen, $C_{1-6}$alkyl or halo;

$R^3$ and $R^4$ each independently are hydrogen, halo, amino, nitro or trifluoromethyl;

Y is hydrogen, nitro, amino, mono- or di($C_{1-6}$alkyl)amino, $C_{1-6}$alkylcarbonylamino, $C_{1-6}$alkyl, $C_{1-6}$alkylcarbonyl, hydroxy, halo, mono- or di-($C_{1-6}$alkyl)aminosulfonyl or a hetercyclic radical of formula

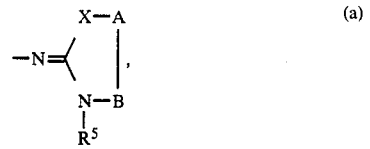

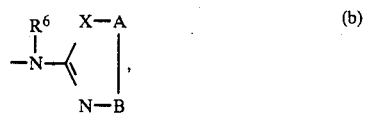

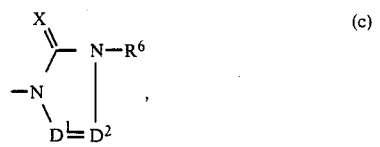

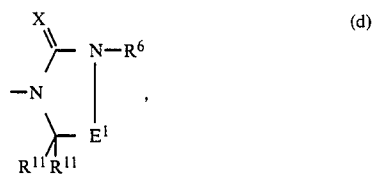

-continued

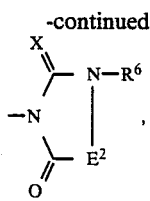 (e)

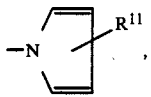 (f)

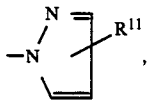 (g)

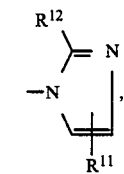 (h)

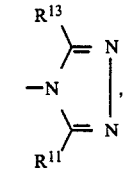 (i)

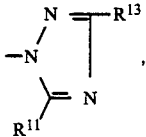 (j)

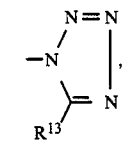 (k)

X is oxygen or sulfur;

$R^5$ and $R^6$ each independently are $C_{1-6}$alkyl, $C_{3-6}$alkenyl, $C_{3-6}$alkynyl, aryl, (aryl)$C_{1-6}$alkyl, $C_{3-7}$cycloalkyl, ($C_{3-7}$cycloalkyl)$C_{1-6}$alkyl, $C_{1-6}$alkyloxy$C_{1-6}$alkyl, mono-, di- or trihalo$C_{1-6}$alkyl; said $C_{1-6}$alkyl, $C_{3-7}$cycloalkyl, ($C_{3-7}$cycloalkyl)$C_{1-6}$alkyl and (aryl)$C_{1-6}$alkyl being optionally substituted with oxo or hydroxy on any carbon atom of the $C_{1-6}$alkyl or $C_{3-7}$cycloalkyl moiety, provided that said carbon atom is not adjacent to the nitrogen atom bearing said $R^5$ or $R^6$ radical; and $R^6$ may also be hydrogen;

A is —C($R^7$)($R^8$)— and B is —CH$_2$— or —CH$_2$—CH$_2$—, or A and B taken together form a bivalent radical of formula —CH=CH— (l) or —CH=N— (m), wherein the carbon atom of said radical is connected to X;

$R^7$ and $R^8$ each independently are hydrogen or $C_{1-6}$alkyl and $R^7$ may also be $C_{1-6}$alkyloxy; and in each of the bivalent radicals —B—, —CH=CH— (l) and —CH=N— (m) one or where possible two hydrogen atoms may be replaced by $C_{1-6}$alkyl or aryl; and in the bivalent radical B, two geminal hydrogen atoms may also be replaced by $C_{4-6}$alkanediyl optionally substituted with one or two $C_{1-6}$alkyl radicals;

$D^1$ is —N= or —CH=; and
$D^2$ is =N—, =CH— or =CH—C(=O)—;
$E^1$ is —CH$_2$—, —CH$_2$—CH$_2$— or —C(=O)—;
$E^2$ is —C($R^9$)($R^{10}$)— or —NR$^{11}$—C(=O)— wherein the carbonyl of said radical is connected to NR$^6$;

$R^9$ and $R^{10}$ are each independently hydrogen or $C_{1-6}$alkyl; or $R^9$ and $R^{10}$ taken together may form a bivalent $C_{4-6}$alkanediyl radical optionally substituted with one or two $C_{1-6}$alkyl radicals; or $R^6$ and $R^9$ taken together may form a bivalent $C_{3-6}$alkanediyl radical optionally substituted with one or two $C_{1-6}$alkyl radicals; and in each of the bivalent radicals $D^1$, $D^2$ and $E^1$, one or where possible two hydrogen atoms may be replaced by $C_{1-6}$alkyl;

each $R^{11}$ independently is hydrogen or $C_{1-6}$alkyl;
$R^{12}$ is hydrogen, $C_{1-6}$alkyl or $C_{1-6}$alkylthio;
$R^{13}$ is hydrogen or $C_{1-6}$alkylthio; and
aryl is phenyl optionally substituted with one to three radicals independently selected from halo, $C_{1-6}$alkyl, $C_{1-6}$alkyloxy, hydroxy or mono-, di- or trihalo$C_{1-6}$alkyl.

2. A method according to claim 1 wherein Y is a radical of formula (a), (b), (c), (d), or (e); and $R^5$ and $R^6$, each independently, are $C_{1-6}$alkyl, $C_{3-7}$cycloalkyl, or (aryl)$C_{1-6}$alkyl all being optionally substituted with oxo or hydroxy on the $C_{1-6}$alkyl or $C_{3-7}$cycloalkyl moiety; or $R^5$ and $R^6$, each independently, are $C_{1-6}$alkyloxy$C_{1-6}$alkyl or mono-, di-, or trihalo$C_{1-6}$alkyl.

3. A method according to claim 2 wherein when:
Y is a radical of formula (a), $R^5$ is $C_{1-6}$alkyl and A-B is CH=CH, (CH$_2$)$_3$, or C(CH$_3$)$_2$—CH$_2$;
Y is a radical of formula (b), $R^6$ is $C_{1-6}$alkyl and A-B is CH$_2$—CH$_2$ wherein one or two hydrogen atoms may be replaced by $C_{1-6}$alkyl or two geminal hydrogen atoms may be replaced by $C_{4-6}$alkanediyl;
Y is a radical of formula (c), X is O, $R^6$ is $C_{1-6}$alkyl, (aryl)$C_{1-6}$alkyl, $C_{3-7}$cycloalkyl, or mono-, di-, or trihalo$C_{1-6}$alkyl; said $C_{1-6}$alkyl, (aryl)$C_{1-6}$alkyl, and $C_{3-7}$cycloalkyl being optionally substituted with oxo or hydroxy on the $C_{1-6}$alkyl or $C_{3-7}$cycloalkyl moiety; and $D^1$=$D^2$ is CH=N wherein hydrogen may be replaced by $C_{1-6}$alkyl;
Y is a radical of formula (d), X is O, $R^6$ is $C_{1-6}$alkyl or (aryl)$C_{1-6}$alkyl both being optionally substituted with oxo or hydroxy on the $C_{1-6}$alkyl moiety; and
Y is a radical of formula (e) and $R^6$ is $C_{1-6}$alkyl or (aryl)$C_{1-6}$alkyl both being optionally substituted with oxo or hydroxy on the $C_{1-6}$alkyl moiety.

4. A method according to claim 3 wherein the chemical compound of Formula (I) is selected from:
2,4-dihydro-4-[4-[4-(4-hydroxy-3,5-dimethyl-phenyl)-1-piperazinyl]phenyl]-5-methyl-2-(1-methylpropyl)-3H-1,2,4-triazol-3-one;
2,4-dihydro-4-[4-[4-(4-hydroxy-phenyl)-1-piperazinyl]phenyl]-5-methyl-2-(1-methylpropyl)-3H-1,2,4-triazol-3-one;
2-[2-(4-bromophenyl)-1-methyl-2-oxoethyl]-2,4-dihydro-4-[4-[4-(4-hydroxy-3,5-dimethylphenyl)-1-piperazinyl]phenyl]-5-methyl-3H-1,2,4-triazol-3-one;
2-[2-(4-bromophenyl)-1-methyl-2-oxoethyl]-2,4-dihydro-4-[4-[4-(4-hydroxyphenyl)-1-piperazinyl]-phenyl]-5-methyl-3H-1,2,4-riazol-3-one;

2-[2-(4-bromophenyl)-2-hydroxy-1-methylethyl]-2,4-dihydro-4-[4-[4-(4-hydroxyphenyl)-1-piperazinyl]phenyl]-5-methyl-3H-1,2,4-triazol-3-one; and 2-[2-(4-bromophenyl)-2-hydroxy-1-methylethyl]-2,4-dihydro-4-[4-[4-(4-hydroxy-3,5-dimethylphenyl)-1-piperazinyl]phenyl]-5-methyl-3H-1,2,4-triazol-3-one.

5. A chemical compound of claim 4 selected from:

2,4-dihydro-4-[4-[4-(4-hydroxy-3,5-dimethyl-phenyl)-1-piperazinyl]phenyl]-5-methyl-2-(1-methyl-propyl)-3H-1,2,4-triazol-3-one;

2-[2-(4-bromophenyl)-1-methyl-2-oxoethyl]-2,4-dihydro-4-[4-[4-(4-hydroxy-3,5-dimethylphenyl)-1-piperazinyl]phenyl]-5-methyl-3H-1,2,4-triazol-3-one; and 2-[2-(4-bromophenyl)-2-hydroxy-1-methylethyl]-2,4-dihydro-4-[4-[4-(4-hydroxyphenyl)-1-piperazinyl]phenyl]-5-methyl-3H-1,2,4-triazol-3-one.

6. A 5-lipoxygenase inhibiting composition comprising a pharmaceutically acceptable carrier and as active ingredient an effective 5-lipoxygenase inhibiting amount of a compound of the formula:

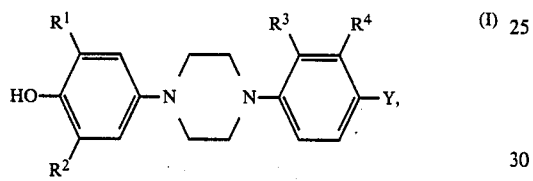 (I)

a pharmaceutically acceptable acid addition salt thereof or a sterochemically isomeric form thereof, wherein:

$R^1$ and $R^2$ each independently are hydrogen, $C_{1-6}$alkyl, or halo;

$R^3$ and $R^4$ each independently are hydrogen, halo, amino, nitro, or trifluoromethyl;

Y is hydrogen, nitro, amino, mono- or di($C_{1-6}$alkyl)amino, $C_{1-6}$alkylcarbonylamino, $C_{1-6}$alkyl, $C_{1-6}$alkylcarbonyl, hydroxy, halo, mono- or di-($C_{1-6}$alkyl)aminosulfonyl, or a heterocyclic radical of the formula:

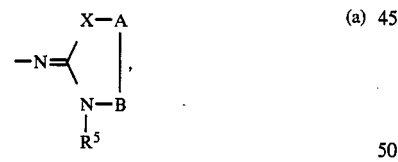 (a)

 (b)

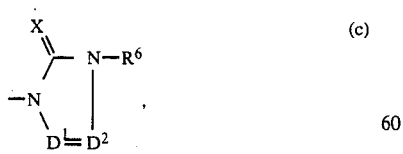 (c)

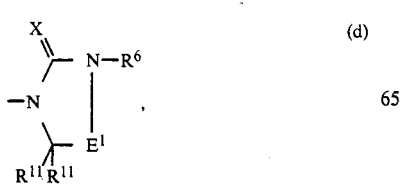 (d)

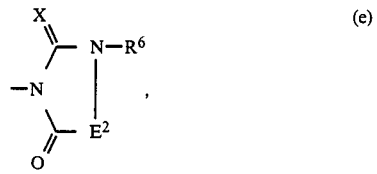 (e)

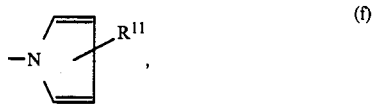 (f)

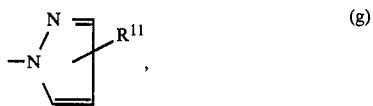 (g)

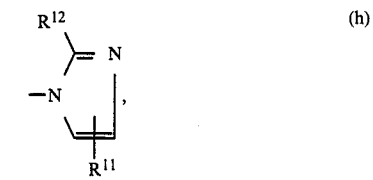 (h)

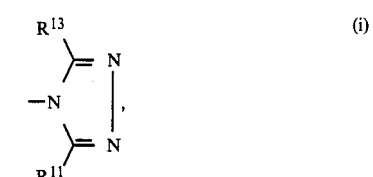 (i)

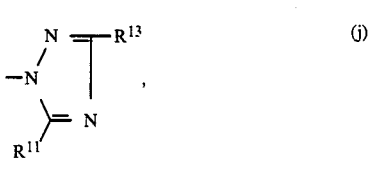 (j)

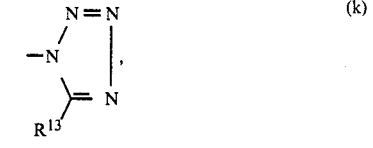 (k)

wherein:

X is oxygen or sulfur;

$R^5$ and $R^6$ each independently are $C_{1-6}$alkyl, $C_{3-6}$alkenyl, $C_{3-6}$alkynyl, aryl, (aryl)$C_{1-6}$alkyl, $C_{3-7}$cycloalkyl, ($C_{3-7}$cycloalkyl)$C_{1-6}$alkyl, $C_{1-6}$alkyloxy$C_{1-6}$alkyl, mono-, di-, or trihalo$C_{1-6}$alkyl; said $C_{1-6}$alkyl, $C_{3-7}$cycloalkyl, ($C_{3-7}$cycloalkyl)$C_{1-6}$alkyl, and (aryl)$C_{1-6}$alkyl being optionally substituted with oxo or hydroxy on any carbon atom of the $C_{1-6}$alkyl or $C_{3-7}$cycloalkyl moiety, provided that said carbon atom is not adjacent to the nitrogen atom bearing said $R^5$ or $R^6$ radical; and $R^6$ may also be hydrogen;

A is —C($R^7$)($R^8$)— and B is —CH$_2$— or —CH$_2$—CH$_2$—, or A and B taken together form a bivalent radical of the formula —CH=CH— (l) or —CH=N— (m), wherein the carbon atom of said radical is connected to X;

$R^7$ and $R^8$ each independently are hydrogen or $C_{1-6}$alkyl and $R^7$ may also be $C_{1-6}$alkyloxy; and in each of the bivalent radicals —B—, —CH=CH— (l) and —CH=N— (m) one or where possible two hydrogen atoms may be replaced by $C_{1-6}$alkyl or aryl; and in the bivalent radical B, two geminal hydrogen atoms may also be replaced by $C_{4-6}$alkanediyl optionally substituted with one or two $C_{1-6}$alkyl radicals;

$D^1$ is —N= or —CH=; and $D^2$ is =N—, =CH— or =CH—C(=O)—;

$E^1$ is —CH$_2$—, —CH$_2$—CH$_2$— or —C(=O)—;

$E^2$ is —C($R^9$)($R^{10}$)— or —NR$^{11}$—C(=O)— wherein the carbonyl of said radical is connected to NR$^6$;

$R^9$ and $R^{10}$ are each independently hydrogen or $C_{1-6}$alkyl; or $R^9$ and $R^{10}$ taken together may form a bivalent $C_{4-6}$alkanediyl radical optionally substituted with one or two $C_{1-6}$alkyl radicals; or $R^6$ and $R^9$ taken together may form a bivalent $C_{3-5}$alkanediyl radical optionally substituted with one or two $C_{1-6}$alkyl radicals; and in each of the bivalent radicals $D^1$, $D^2$, and $E^1$, one or where possible two hydrogen atoms may be replaced by $C_{1-6}$alkyl;

each $R^{11}$ independently is hydrogen $C_{1-6}$alkyl;

$R^{12}$ is hydrogen, $C_{1-6}$alkyl, or $C_{1-6}$alkylthio;

$R^{13}$ is hydrogen or $C_{1-6}$alkylthio; and aryl is phenyl optionally substituted with one to three radicals independently selected from halo, $C_{1-6}$alkyl, $C_{1-6}$alkyloxy, hydroxy, or mono-, di- or trihalo$C_{1-6}$alkyl.

7. The composition of claim 6 wherein Y is a radical of formula (a), (b), (c), (d), or (e); and $R^5$ and $R^6$, each independently, are $C_{1-6}$alkyl, $C_{3-7}$cycloalkyl, or (aryl)$C_{1-6}$alkyl all being optionally substituted with oxo or hydroxy on the $C_{1-6}$alkyl or $C_{3-7}$cycloalkyl moiety; or $R^5$ and $R^6$, each independently, are $C_{1-6}$alkyloxy$C_{1-6}$alkyl or mono-, di-, or trihalo$C_{1-6}$alkyl.

8. The composition of claim 7 wherein when:

Y is a radical of formula (a), $R^5$ is $C_{1-6}$alkyl and A-B is CH=CH, (CH$_2$)$_3$, or C(CH$_3$)$_2$—CH$_2$;

Y is a radical of formula (b), $R^6$ is $C_{1-6}$alkyl and A-B is CH$_2$—CH$_2$ wherein one or two hydrogen atoms may be replaced by $C_{1-6}$alkyl or two geminal hydrogen atoms may be replaced by $C_{4-6}$alkanediyl;

Y is a radical of formula (c), X is O, $R^6$ is $C_{1-6}$alkyl, (aryl)$C_{1-6}$alkyl, $C_{3-7}$cycloalkyl, or mono-, di-, or trihalo$C_{1-6}$alkyl; said $C_{1-6}$alkyl, (aryl)$C_{1-6}$alkyl, and $C_{3-7}$cycloalkyl being optionally substituted with oxo or hydroxy on the $C_{1-6}$alkyl or $C_{3-7}$cycloalkyl moiety; and $D^1$=$D^2$ is CH=N wherein hydrogen may be replaced by $C_{1-6}$alkyl;

Y is a radical of formula (d), X is O, $R^6$ is $C_{1-6}$alkyl or (aryl)$C_{1-6}$alkyl both being optionally substituted with oxo or hydroxy on the $C_{1-6}$alkyl moiety; and Y is a radical of formula (e) and $R^6$ is $C_{1-6}$alkyl or (aryl)$C_{1-6}$alkyl both being optionally substituted with oxo or hydroxy on the $C_{1-6}$alkyl moiety.

9. The composition of claim 8 wherein the compound of Formula (I) is selected from:

2,4-dihydro-4-[4-[4-(4-hydroxy-3,5-dimethyl-phenyl)-1-piperazinyl]phenyl]-5-methyl-2-(1-methylpropyl)-3$\underline{H}$-1,2,4-triazol-3-one;

2,4-dihydro-4-[4-[4-(4-hydroxy-phenyl)-1-piperazinyl]phenyl]-5-methyl-2-(1-methylpropyl)-3$\underline{H}$-1,2,4-triazol-3-one;

2-[2-(4-bromophenyl)-1-methyl-2-oxoethyl]-2,4-dihydro-4-[4-[4-(4-hydroxy-3,5-dimethylphenyl)-1-piperazinyl]phenyl]-5-methyl-3$\underline{H}$-1,2,4-triazol-3-one;

2-[2-(4-bromophenyl)-1-methyl-2-oxoethyl]-2,4-dihydro-4-[4-[4-(4-hydroxyphenyl)-1-piperazinyl]phenyl-5-methyl-3$\underline{H}$-1,2,4-triazol-3-one;

2-[2-(4-bromophenyl)-2-hydroxy-1-methylethyl]-2,4-dihydro-4-[4-[4-(4-hydroxyphenyl)-1-piperazinyl]phenyl]-5-methyl-3$\underline{H}$-1,2,4-triazol-3-one; and 2-[2-(4-bromophenyl)-2-hydroxy-1-methylethyl]-2,4-dihydro-4-[4-[4-(4-hydroxy-3,5-dimethylphenyl)-1-piperazinyl]phenyl]-5-methyl-3$\underline{H}$-1,2,4-triazol-3-one.

10. A compound of the formula:

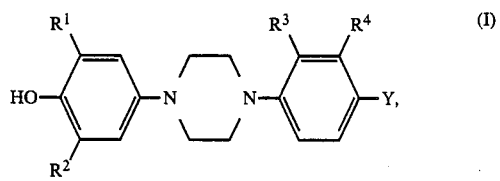

a pharmaceutically acceptable acid addition salt thereof or a sterochemically isomeric form thereof, wherein:

$R^1$ and $R^2$ each independently are hydrogen, $C_{1-6}$alkyl, or halo;

$R^3$ and $R^4$ each independently are hydrogen, halo, amino, nitro, or trifluoromethyl;

Y is hydrogen, nitro, amino, mono- or di($C_{1-6}$alkyl)amino, $C_{1-6}$alkylcarbonylamino, $C_{1-6}$alkyl, $C_{1-6}$alkylcarbonyl, hydroxy, halo, mono- or di($C_{1-6}$alkyl)aminosulfonyl, or a heterocyclic radical selected from a radical of the formula:

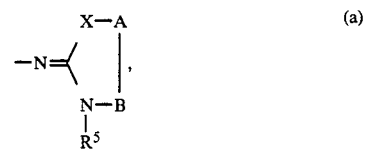

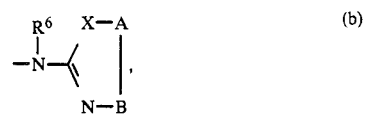

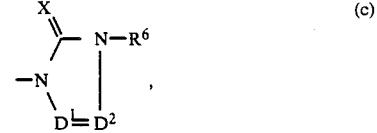

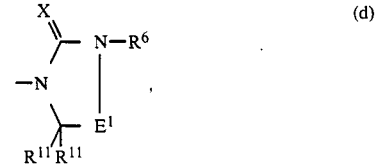

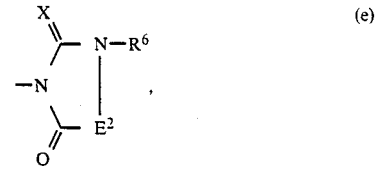

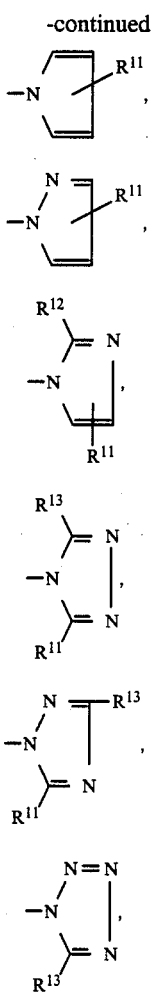

(f)

(g)

(h)

(i)

(j)

(k)

wherein:
X is oxygen or sulfur;
$R^5$ and $R^6$ each independently are $C_{1-6}$alkyl, $C_{3-6}$alkenyl, $C_{3-6}$alkynyl, aryl, (aryl)$C_{1-6}$alkyl, $C_{3-7}$cycloalkyl, ($C_{3-7}$cycloalkyl)$C_{1-6}$alkyl, $C_{1-6}$alkyloxy$C_{1-6}$alkyl, mono-, di-, or trihalo$C_{1-6}$alkyl; said $C_{1-6}$alkyl, $C_{3-7}$cycloalkyl, ($C_{3-7}$cycloalkyl)$C_{1-6}$alkyl, and (aryl)$C_{1-6}$alkyl being optionally substituted with oxo or hydroxy on any carbon atom of the $C_{1-6}$alkyl or $C_{3-7}$cycloalkyl moiety, provided that said carbon atom is not adjacent to the nitrogen atom bearing said $R^5$ or $R^6$ radical; and $R^6$ may also be hydrogen;
A is —C($R^7$)($R^8$)— and B is —CH$_2$— or —CH$_2$—CH$_2$—, or A and B taken together form a bivalent radical of the formula —CH=CH— (l) or —CH=N— (m), wherein the carbon atom of said bivalent radical is connected to X;
$R^7$ and $R^8$ each independently are hydrogen or $C_{1-6}$alkyl and $R^7$ may also be $C_{1-6}$alkyloxy; and in each of the bivalent radicals —B—, —CH=CH— (l), and —CH=N— (m) one or where possible two hydrogen atoms may be replaced by $C_{1-6}$alkyl or aryl; and in the bivalent radical B, two geminal hydrogen atoms may also be replaced by $C_{4-6}$alkanediyl optionally substituted with one or two $C_{1-6}$alkyl radicals;
$D^1$ is —N= or —CH=;
$D^2$ is =N—, =CH—, or =CH—C(=O)—;

$E^1$ is —CH$_2$—, —CH$_2$—CH$_2$—, or —C(=O)—;
$E^2$ is —C($R^9$)($R^{10}$)— or —NR$^{11}$—C(=O)— wherein the carbonyl of said radical is connected to NR$^6$;
$R^9$ and $R^{10}$ are each independently hydrogen or $C_{1-6}$alkyl; or $R^9$ and $R^{10}$ taken together may form a bivalent $C_{4-6}$alkanediyl radical optionally substituted with one or two $C_{1-6}$alkyl radicals; or $R^6$ and $R^9$ taken together may form a bivalent $C_{3-5}$alkanediyl radical optionally substituted with one or two $C_{1-6}$alkyl radicals; and in each of the bivalent radicals $D^1$, $D^2$, and $E^1$, one or where possible two hydrogen atoms may be replaced by $C_{1-6}$alkyl;
each $R^{11}$ independently is hydrogen $C_{1-6}$alkyl;
$R^{12}$ is hydrogen, $C_{1-6}$alkyl, or $C_{1-6}$alkylthio; and
$R^{13}$ is hydrogen or $C_{1-6}$alkylthio,
wherein aryl is phenyl optionally substituted with one to three radicals independently selected from halo, $C_{1-6}$alkyl, $C_{1-6}$alkyloxy, hydroxy, or mono-, di- or trihalo$C_{1-6}$alkyl,
and wherein:
at least one of $R^1$ or $R^2$ is $C_{1-6}$alkyl or halo; or
at least one of $R^3$ or $R^4$ is halo, amino, nitro, or trifluoromethyl; or
Y is mono- or di($C_{1-6}$alkyl)amino, ($C_{1-6}$alkyl)carbonylamino, $C_{1-6}$alkyl, $C_{1-6}$alkylcarbonyl, halo, mono- or di($C_{1-6}$alkyl)aminosulfonyl, or a radical selected from radicals of the formula:

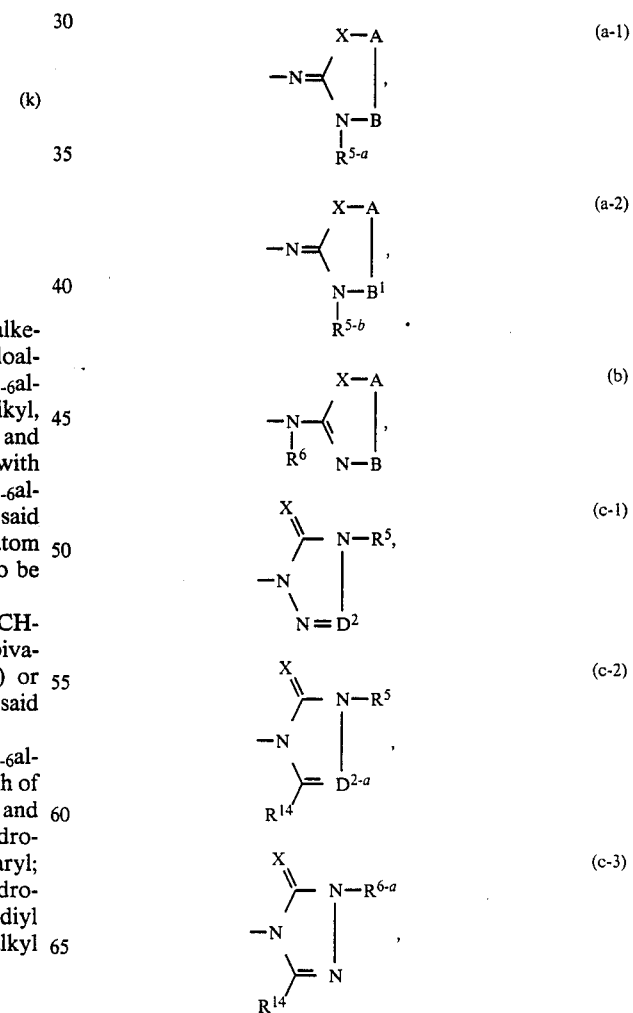

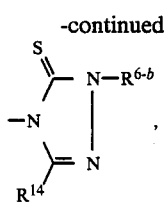 (c-4)

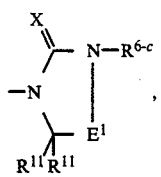 (d-1)

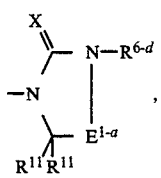 (d-2)

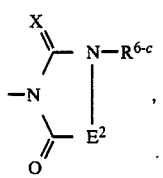 (e-1)

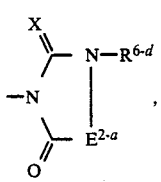 (e-2)

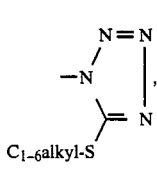 (k-1)

wherein:

$R^{5-a}$ is a mono-, di-, or trihalo$C_{1-6}$alkyl; or a $C_7$cycloalkyl or ($C_7$cycloalkyl)$C_{1-6}$alkyl, both being optionally substituted with oxo or hydroxy on the $C_{1-6}$alkyl or $C_7$cycloalkyl moiety;

$R^{5-b}$ is $C_{1-6}$alkyl, $C_{3-6}$cycloalkyl, ($C_{3-6}$cycloalkyl)$C_{1-6}$alkyl, or (aryl)$C_{1-6}$alkyl, all being substituted with oxo or hydroxy on the $C_{1-6}$alkyl or $C_{3-6}$cycloalkyl moiety;

$B^1$ is —$CH_2$—$CH_2$— wherein one or two hydrogen atoms may be replaced by $C_{1-6}$alkyl or aryl, or two geminal hydrogen atoms may be replaced by a $C_{4-6}$alkanediyl radical optionally substituted with one or two $C_{1-6}$alkyl radicals;

$D^{2-a}$ is =CH— or =CH—C(=O)— wherein the hydrogen atom may be replaced by $C_{1-6}$alkyl;

$R^{14}$ is hydrogen or $C_{1-6}$alkyl;

$R^{6-a}$ is $C_{3-6}$alkenyl, $C_{3-6}$alkynyl, aryl, $C_{3-7}$cycloalkyl, ($C_{3-7}$cycloalkyl)$C_{1-6}$alkyl, $C_{1-6}$alkyloxy$C_{1-6}$alkyl, mono-, di-, or trihalo$C_{1-6}$alkyl; $C_7$cycloalkyl or ($C_7$cycloalkyl)$C_{1-6}$alkyl, both being substituted with oxo or hydroxy on the $C_{1-6}$alkyl or $C_7$cycloalkyl moiety;

$R^{6-b}$ is $C_{1-6}$alkyl, (aryl)$C_{1-6}$alkyl; or $C_{1-6}$alkyl, $C_{3-6}$cycloalkyl, ($C_{3-6}$cycloalkyl)$C_{1-6}$alkyl, or (aryl)$C_{1-6}$alkyl being substituted with oxo or hydroxy on the $C_{1-6}$alkyl or $C_{3-6}$cycloalkyl moiety;

$R^{6-c}$ is mono-, di-, or trihalo$C_{1-6}$alkyl; or $C_7$cycloalkyl or ($C_7$cycloalkyl)$C_{1-6}$alkyl, both being optionally substituted with oxo or hydroxy on the $C_{1-6}$alkyl or $C_7$cycloalkyl moiety; or $R^{6-c}$ and $R^9$ taken together may form a bivalent $C_{3-5}$alkanediyl radical optionally substituted with one or two $C_{1-6}$alkyl radicals;

$E^{1-a}$ is —$CH_2$—$CH_2$— wherein one or two hydrogen atoms may be replaced by $C_{1-6}$alkyl;

$R^{6-d}$ is $C_{1-6}$alkyl, $C_{3-6}$cycloalkyl, ($C_{3-6}$cycloalkyl)$C_{1-6}$alkyl, or (aryl)$C_{1-6}$alkyl being substituted with oxo or hydroxy on the $C_{1-6}$alkyl or $C_{3-6}$cycloalkyl moiety; and $E^{2-a}$ is —$NR^{11}$—C(=O)l, wherein aryl is as defined above.

11. A chemical compound according to claim 10 wherein at least one of $R^1$ or $R^2$ is $C_{1-4}$alkyl or halo; or at least one of $R^3$ or $R^4$ is halo, amino, nitro or trifluoromethyl; or Y is a radical of formula

 (b-1)

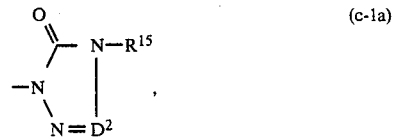 (c-1a)

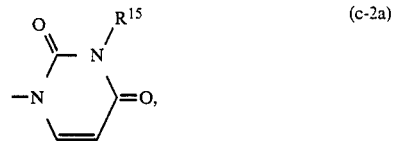 (c-2a)

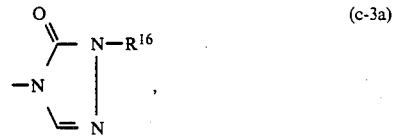 (c-3a)

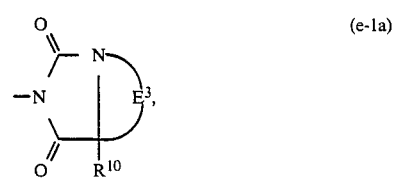 (e-1a)

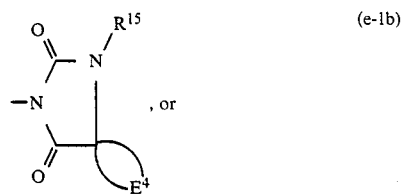 (e-1b)

, or

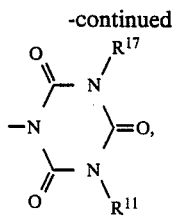 (e-2a)

wherein A is —C(R$^7$)(R$^8$)— and B is —CH$_2$— or —CH$_2$—CH$_2$—, or A and B taken together form a bivalent radical of formula —CH=CH— (l) or —CH=N— (m), wherein the carbon atom of said radical is connected to X;

R$^7$ and R$^8$ each independently are hydrogen or C$_{1-6}$alkyl and R$^7$ may also be C$_{1-6}$alkyloxy; and in each of the bivalent radicals —B—, —CH=CH— (l) and —CH=N— (m) one or where possible two hydrogen atoms may be replaced by C$_{1-6}$alkyl or aryl; and in the bivalent radical B, two geminal hydrogen atoms may also be replaced by C$_{4-6}$alkanediyl optionally substituted with one or two C$_{1-6}$alkyl radicals;

D$^2$ is =N—, =CH— or =CH—C(=O)—; wherein one or where possible two hydrogen atoms may be replaced by C$_{1-6}$alkyl;

R$^{10}$ is hydrogen or C$_{1-6}$alkyl;
R$^{11}$ is hydrogen or C$_{1-6}$alkyl;
R$^{15}$ is C$_{1-6}$alkyl;
R$^{16}$ is mono-, di- or trihaloC$_{1-6}$alkyl; C$_{3-6}$cycloalkyl; or C$_7$cycloalkyl optionally substituted with oxo;
E$^3$ is C$_{3-5}$alkanediyl;
E$^4$ is C$_{4-6}$alkanediyl;
R$^{17}$ is (aryl)C$_{1-6}$alkyl substituted with oxo or hydroxy on the C$_{1-6}$alkyl moiety.

12. A chemical compound according to claim 11 wherein at least one of R$^1$ or R$^2$ is methyl, or Y is a radical of formula (c-3a), (e-1a) or (e-2a).

* * * * *

UNITED STATES PATENT AND TRADEMARK OFFICE
CERTIFICATE OF CORRECTION

PATENT NO. : 4,931,444

DATED : June 5, 1990

INVENTOR(S) : Jean P. F. Van Wauwe, et al.

It is certified that error appears in the above-identified patent and that said Letters Patent is hereby corrected as shown below:

Col. 46, line 15, should be (1-a), not (I)

Signed and Sealed this

Ninth Day of June, 1992

Attest:

DOUGLAS B. COMER

*Attesting Officer*  *Acting Commissioner of Patents and Trademarks*